(12) United States Patent
Cibelli et al.

(10) Patent No.: US 7,696,404 B2
(45) Date of Patent: Apr. 13, 2010

(54) EMBRYONIC OR STEM-LIKE CELL LINES PRODUCED BY CROSS SPECIES NUCLEAR TRANSPLANTATION AND METHODS FOR ENHANCING EMBRYONIC DEVELOPMENT BY GENETIC ALTERATION OF DONOR CELLS OR BY TISSUE CULTURE CONDITIONS

(75) Inventors: Jose Cibelli, East Lansing, MI (US); Michael D. West, Mill Valley, CA (US)

(73) Assignee: Advanced Cell Technology, Inc., Worcester, MA (US)

( * ) Notice: Subject to any disclaimer, the term of this patent is extended or adjusted under 35 U.S.C. 154(b) by 1563 days.

(21) Appl. No.: 10/329,979

(22) Filed: Dec. 27, 2002

(65) Prior Publication Data

US 2003/0229908 A1    Dec. 11, 2003

Related U.S. Application Data

(63) Continuation-in-part of application No. 09/467,076, filed on Dec. 20, 1999, now abandoned, which is a continuation-in-part of application No. 09/395,368, filed on Sep. 14, 1999, now abandoned, which is a continuation-in-part of application No. 09/260,468, filed on Mar. 2, 1999, now abandoned, which is a continuation-in-part of application No. 09/032,945, filed on Mar. 2, 1998, now abandoned, which is a continuation-in-part of application No. 08/699,040, filed on Aug. 19, 1996, now abandoned, said application No. 09/467,076 filed as application No. PCT/US99/04608 on Mar. 2, 1999, application No. 10/329,979, is a continuation-in-part of application No. 09/685,061, filed on Oct. 6, 2000, which is a continuation-in-part of application No. 09/260,468, filed on Mar. 2, 1999, application No. 10/329,979, which is a continuation-in-part of application No. 09/874,040, filed on Jun. 6, 2001, which is a continuation-in-part of application No. 08/699,040, filed on Aug. 19, 1996, application No. 10/329,979, which is a continuation-in-part of application No. 09/809,018, filed on Mar. 16, 2001, which is a continuation-in-part of application No. 09/032,945, filed on Mar. 2, 1998.

(60) Provisional application No. 60/342,358, filed on Dec. 27, 2001, provisional application No. 60/357,848, filed on Feb. 21, 2002.

(51) Int. Cl.
*C12N 15/00* (2006.01)
*C12N 5/02* (2006.01)

(52) U.S. Cl. .................................. 800/24; 435/377

(58) Field of Classification Search .............. 435/377, 435/366, 325; 800/24
See application file for complete search history.

(56) References Cited

U.S. PATENT DOCUMENTS

| 4,944,384 | A | 7/1990 | Herron |
|---|---|---|---|
| 4,994,384 | A | 2/1991 | Prather et al. |
| 4,997,384 | A | 3/1991 | Godfrey et al. |
| 5,057,420 | A | 10/1991 | Massey |
| 5,096,822 | A | 3/1992 | Rosenkrans, Jr. et al. |
| 5,262,409 | A | 11/1993 | Margolis et al. |
| 5,464,764 | A | 11/1995 | Capecchi et al. |
| 5,496,720 | A | 3/1996 | Susko-Parrish et al. |
| 5,631,153 | A | 5/1997 | Capecchi et al. |
| 5,646,008 | A | 7/1997 | Thompson et al. |
| 5,681,718 | A | 10/1997 | Field |
| 5,698,446 | A | 12/1997 | Klump |
| 5,712,156 | A | 1/1998 | Fry |
| 5,716,827 | A | 2/1998 | Tsukamoto et al. |
| 5,843,780 | A | 12/1998 | Thomson |
| 5,905,042 | A | 5/1999 | Stice et al. |
| 6,200,806 | B1 * | 3/2001 | Thomson ............... 435/366 |

FOREIGN PATENT DOCUMENTS

| WO | WO-90/03432 | 4/1990 |
|---|---|---|
| WO | WO-91/08216 | 6/1991 |

(Continued)

OTHER PUBLICATIONS

Westhusin, ME et al. Theriogenology 46:243-252, 1996.*

(Continued)

*Primary Examiner*—Thaian N Ton
*Assistant Examiner*—Marcia S Noble
(74) *Attorney, Agent, or Firm*—Hunton & Williams

(57) ABSTRACT

An improved method of nuclear transfer involving the transplantation of differentiated donor cell nuclei into enucleated oocytes of a species different from the donor cell is provided. The resultant nuclear transfer units are useful for the production of isogenic embryonic stem cells, in particular human isogenic embryonic or stem cells. These embryonic or stem-like cells are useful for producing desired differentiated cells and for introduction, removal or modification, of desired genes, e.g., at specific sites of the genome of such cells by homologous recombination. These cells, which may contain a heterologous gene, are especially useful in cell transplantation therapies and for in vitro study of cell differentiation. Also, methods for improving nuclear transfer efficiency by genetically altering donor cells to inhibit apoptosis, select for a specific cell cycle and/or enhance embryonic growth and development are provided.

4 Claims, 3 Drawing Sheets

FOREIGN PATENT DOCUMENTS

| | | |
|---|---|---|
| WO | WO-94/24274 | 10/1994 |
| WO | WO-94/26884 | 11/1994 |
| WO | WO-94/26889 | 11/1994 |
| WO | WO-97/07669 | 3/1997 |
| WO | WO-99/04608 | 1/1999 |
| WO | WO-99/05266 | 2/1999 |
| WO | WO-00/29602 | 5/2000 |
| WO | WO-01/00793 | 1/2001 |
| WO | WO-01/19977 | 3/2001 |
| WO | WO-01/46401 | 6/2001 |

OTHER PUBLICATIONS

Westhusin, ME et al Theriogenology 55:35-49, 2001.*
Dinnyes, A et al. Cloning Stem Cells 4(1):81-90, 2002.*
Collas, P. and FL Barnes. Mol Reprod Dev 38:264-267, 1994.*
Wolfe, BA, et al. Theriogenology 33(1):350, 1990.*
Dominko, T et al. Biol Reprod 60:1496-1502, 1999.*
Hua, S et a. Anim Reprod Sci (2007), doi:10.1016/j.anireprosci.2007. 03.002 (p. 1-13).*
Simerly, C et al. Science 300:297, 2003.*
Vogel, G. Science 300:225-226, 2003.*
Bergeron, et al., "Defects in Regulation of Apoptosis in Caspase-2-Deficient Mice," Genes & Development, 12:1304-1314 (1998).
Blerkom Van J., et al., "Mitochondrial Transfer Between Oocytes: Potential Applications of Mitochondrial Donation and the Issue of Heteroplasmy," Human Reproduction, 13(10):2857-2868 (1998).
Bordignon, V., et al., "Telophase Enucleation: An Improved Method to Prepare Recipient Cytoplasts for Use in Bovine Nuclear Transfer," Molecular Reproduction and Development, 49: 29-36 (1998).
Botz, J., et al., "Cell Cycle Regulation of the Murine Cyclin E Gene Depends on an E2F Binding Site in the Promoter," Molecular and Cellular Biology, 16(7):3401-3409 (1996).
Cai, et al., "Sequence and Transcription of Qa-2-Encoding Genes in Mouse Lymphocytes and Blastocysts," Immunogenetics, 45(2):97-107 (1996).
Campbell, et al., "Totipotency or Multipotentiality of Cultured Cells: Applications and Processes, Therigenology 47:63-72 (1997).
Chesne, P., et al., "Nuclear Transfer in Cattle: Birth of Cloned Calves and Estimation of Blastomere Totipotency in Morulae Used as a Source of Nuclei," Life Sciences, 316:487-491.
Karnikova, L., et al., "Mouse Oocyte Maturation: the Effect of Modified Nucleocytoplasmic Ratio," Reprod. Nutr. Dev. 38(6):665-670 (1998).
Lanza, R. P., et al. "Human Therapeutic Cloning," Nature Medicine, 5(9):975-977 (1999).
Liu, et al., "Interplay of Maturation-Promoting Factor and Mitogen-Activated Protein Kinase Inactivation during Metaphase-to-Interphase Transition of Activated Bovine Oocytes." Biology of Reproduction, 61:1-7 (1999).
Meirelles, et al., "Complete Replacement of the Mitochondrial Genotype in a *Bos indicus* Calf Reconstructed by Nuclear Transfer to a *Bos taurus* Oocyte," Genetics, 158:351-356 (2001).
Meirelles, F.V., et al., "Mitochondrial Genotype Segregation During Preimplantation Development in Mouse Heteroplasmic Embryos," Genetics, 148:877-883 (1998).
Mitalipova, M., et al., "Bovine Oocyte Cytoplasm Reprograms Somatic Cell Nuclei from Various Mammalian Species," Theriogenology, 49(1):389 (1998).
Rime, et al., "6-Dimethylaminopurine (6-DMAP), A Reversible Inhibitor of the Transition to Metaphase during the First Meiotic Cell Division of the Mouse Oocyte," Developmental Biology, 133(1):169-179 (1989).
Shitara, et al., "Selective and Continuous Elimination of Mitochondria Microinjected Into Mouse Eggs from Spermatids, but Not From Liver Cells, Occurs Throughout Embryogenesis," Genetics, 156:1277-1284 (2000).
Sims, M., et al., "Production of Calves by Transfer of Nuclei from Cultured Inner Cell Mass Cells," Proceedings of the National Academy of Sciences of USA, 90(13):6143-6147 (1993).
Stedman, Stedman's Medical Dictionary, 1995, Williams & Wilkins, Baltimore, MD, 21201, USA, p. 1642.
Thomson, J. A., et al., "Neural Differentiation of Rhesus Embryonic Stem Cells," APMIS, 106:149-157 (1998).
Thomson, J. A., et al., "Pluripotent Cell Lines Derived from Common Marmoset (*Callithrix jacchus*) Blastocysts," Biology of Reproduction, 55:254-259 (1996).
Trounson, et al., "Potential Benefits of Cell Cloning for Human Medicine," Reproduction Fertility and Development, 10:121-125 (1998).
Zawada, W. M., et al., "Somatic Cell Cloned Transgenic Bovine Neurons for Transplantation in Parkinsonian Rats," Nature Medicine, 4(5):569-574 (1998).
www.advancedcell.com/2000-10-08.htm, Press release on Oct. 8, 2000 by Advanced Cell Technology, "Nearly Extinct Ox-Like Gaur Due to be Born in November," 2 pgs.
www.advancedcell.com/2001-01-12.htm. Press release on Jan. 12, 2001 by Advanced Cell Technology,"Advanced Cell Technology Announces Birth of First Cloned Endangered Species" 2 pgs.
www.advancedcell.com/2003-04-08.htm, Press release on Apr. 8, 2003 by Advanced Cell Technology, "Collaborative Effort Yields Endangered Species Clone" 3 pgs.
U.S. Appl. No. 08/699,040, Robl et al.
U.S. Appl. No. 09/032,945, Robl et al.
U.S. Appl. No. 09/260,468, Robl. et al.
U.S. Appl. No. 09/395,368, Robl et al.
U.S. Appl. No. 09/467,076, Cibelli et al.
U.S. Appl. No. 09/685,061, Robl et al.
U.S. Appl. No. 09/809,018, filed Aug. 9, 2001, Robl et al.
U.S. Appl. No. 09/874,040, filed Dec. 19, 2002, Robl et al.
U.S. Appl. No. 60/342,359, Cibelli et al.
U.S. Appl. No. 60/357,848, West et al.
Adams, J. and Cory, S., "The Bcl-2 protein family: Arbiters of cell survival," Science, 281(5381):1322-1326(1998).
Adenot et al., "Differential H4 acetylation of paternal and maternal chromatin precedes DNA replication and differential transcriptional activity in pronuclei of 1-cell mouse embryos," Development, 124:4615-4625(1997).
Arsenian et al., "Serum response factor is essential for mesoderm formation during mouse embryogenesis," The EMBO Journal, 17(21):6289-6299(1998).
Bain et al., "Embryonic Stem Cells Express Neuronal Properties in Vitro," Dev. Biol., 168:342-357(1995).
Barnes et al., "Influence of Recipient Oocyte Cell Cycle Stage on DNA Synthesis, Nuclear Envelope Breakdown, Chromosome Constitution, and Development in Nuclear Transplant Bovine Embryos," Mol. Reprod. and Biol., 36:33-41(1993).
Bouchie et al., "Business and Regulatory News Briefs," Nature Biotech., 21:473-475(2003).
Bowen, C.C., and Wilson, G.B., "A comparison of the effects of several antimitotic agents," Journal of Heredity, 45:3-9(1954).
Bradley et al., "Formation of Germ-Like Chimaeras from Embryo-Derived Teratocarcinoma Cell Lines," Nature, 309:255-256(1984).
Campbell et al., "Production of Live Lambs Following Nuclear Transfer of Cultured Embryonic Disc Cells," Theriogenology, 43:181(1995).
Campbell et al., "Sheep Cloned by Nuclear Transfer from a Cultured Cell Line," Nature, 380:64-66(1996).
Chen et al., "Disruption of the HNF-4 gene, expressed in visceral endoderm, leads to cell death in embryonic ectoderm and impaired gastrulation of mouse embryos," Genes Devel., 8(20):2466-77(1994).
Chen et al., "Embryonic Stem Cells Generated by Nuclear Transfer of Human Somatic Nuclei into Rabbit Oocytes," Cell Research, 13(4):251-263(2003).
Cheong et al., "Birth of Mice After Transplantation of Early Cell-Cycle-Stage Embryonic Nuclei into Enucleated Oocytes," Biol. Reprod., 48:958-963(1993).
Cherny, R. and Merei, J., "Evidence for Pluripotency of Bovine Primordial Germ Cell-Derived Cell Lines Maintained in Long-Term Culture," Theriogenology, 41:175(1994).
Cibelli et al., "Cloned transgenic calves produced from nonquiescent fetal fibroblasts," Science, 280(5367):1256-1258(1998).

Collas, P., and Barnes, F., "Nuclear Transplantation by Microinjection of Inner Cell Mass and Granulosa Cell Nuclei," Molecular Reproduction and Development, 38(3):264-267(1994).

Dennis, "Chinese Fusion Method Promises Fresh Route to Human Stem Cells," Nature, 424:711(2003).

DiBerardino, "Genetic Stability and Modulation of Metazoan Nuclei Transplanted into Eggs and Oocytes," Differentiation, 17:17-30(1980).

Dominko et al., "Bovine Oocyte as a Universal Recipient Cytoplasm in Mammalian Nuclear Transfer," Theriogenology, 49(1):385(1999).

Dominko et al., "Bovine Oocyte Cytoplasm Supports Development of Embryos Produced by Nuclear Transfer of Somatic Cell Nuclei from Various Mammalian Species," Biol. Of Reprod., 60:1496-1502(1999).

Evans et al., "Establishment in culture of pluripotential cells from mouse embryos," Nature, 29:154-156(1981).

Eistetter, "Pluripotent Embryonal Stem Cell Lines Can Be Established from Disaggregated Mouse Morulae," Develop. Growth & Differ., 31(3):275-282(1989)

First, N., and Prather, R., "Genomic potential in mammals," Differentiation, 48:1-8(1991).

Gandolfi et al., "The Maternal Legacy to the Embryo: Cytoplasmic Components and Their Effects on Early Development," Theriogenology, 55(6):1255-76(2001).

Gerfen et al., "Isolation of Embryonic Cell-Lines From Porcine Blastocysts," Anim. Biotech., 6(1):1-14(1995).

Graham, Christopher., "The Fusion of Cells with One- and Two-Cell Mouse Embryos," Wister Inot. Symp. Monogr., 9:19-35(1969).

Granerus et al., "Growth factors and apoptosis," Cell Prolif., 29:306-314(1996).

Handyside et al., "Towards the Isolation of Embryonal Stem Cell Lines From the Sheep," Roux's Arch Dev. Biol. 196:185-190(1987).

Heyman et al., "Cloning of Domestic Species," Animal Reprod. Science, 42(1/4):427-436(1994).

Holdener et al., "msd is required for mesoderm induction in mice," Development, 120:1335-1346(1994).

Huang, "The Potential of Stem Cells," MURJ, 6:49-51(2002).

Jaenisch et al., "Treatment of mice with 5-azacytidine efficiently activates silent retroviral genomes in different tissues," Proc. Natl. Acad. Sci. USA, 82:1451-1455(1985).

Jones et al., "Evolution of a cultural protocol for successful blastocyst development and pregnancy," Human Reproduction, 13(1):169-177(1998).

Juriscova et al., "Expression and Regulation of Genes Associated With Cell Death During Murine Preimplantation Embryo Development," Molecular Reproduction and Development, 51:243-253(1998).

Keefer et al., "Bovine Inner Cell Mass Cells as Donor Nuclei in the Production of Nuclear Transfer Embryos and Calves," Biol. Reprod., 50:935-939(1994).

Kenyon et al., "Expanding the Functional Human Mitochondrial DNA Database by the Establishment of Primate Xenomitochondrial Cybrids," Proc. Natl. Acad. Sci. USA, 94:9131-9135(1997).

King et al., "Mutagenic Analysis of the Destruction Signal of Mitotic Cyclins and Structural Characterization of Ubiquitinated Intermediates," Molecular Biology the Cell, 7:1343-1357(1996).

Lee et al., "RNA helicase A is essential for normal gastrulation," Proc. Natl. Acad. Sci. USA, 95:13709-13713(1998).

Loi et al., "Development of Parthenogenetic and Cloned Ovine Embryos: Effe of Activation Protocols," Biol. Reprod., 58(5):1177-87(1998).

Loi et al., "Genetic Rescue of an Endangered Mammal by Cross-Species Nuclear Transfer Using Post-Mortem Somatic Cells," Nature Biotech., 19:962-964(2001).

Lundberg et al., "Generation of DOPA-Producing Astrocytes by Retroviral Transduction of the Human Tyrosine Hydroxylase Gene: in vitro Characterization and in vivo Effects in the Rat Parkinson Model," Developmental Neurology, 139:39-53(1996).

Marshall, "Claim of Human-Cow Embryo Greeted With Skepticism," Science, 282:1390-1391(1998).

Martin, "Isolation of a Pluripotent Cell Line from Early Mouse Embryos Cultured in Medium Conditioned by Teratocarcinoma Stem Cells," Proc. Natl. Acad. Sci. USA, 78(12):7634-7638(1981).

Modlinski et al., "Embryonic stem cells: developmental capabilities and their possible use in a mammalian embryo cloning," Animal Reprod. Sci,. 42(1/4):437-446(1996).

Morrisey et al., "GATA6 regulates HNF4 and is required for differentiation of visceral endoderm in the mouse embryo," Genes & Devel., 12:3579-3590(1998).

Mulligan, "The Basic Science of Gene Therapy," Science, 260:926-932(1993).

Notarianni et al., "Derivation of pluripotent, embryonic cell lines from the pig and sheep," J. Reprod. Fert., Suppl. 43:255-260(1991).

Notarianni et al., "Maintenance and differentiation in culture of pluripotential embryonic cell lines from pig blastocysts," J. Reprod. Fert. Suppl. 41:51-56(1990).

Palacios et al., "In vitro Generation of Hematopoietic Stem Cells from an Embryonic Stem Cell Line," Proc. Natl. Acad. Sci. USA, 92:7530-7534(1995).

Pederson, "Studies of in vitro Differentiation with Embryonic Stem Cells," J. Reprod. Fert. Devel., 6:543-552(1994).

Radice et al., "Hβ58, an insertional mutation affecting early postimplantation development of the mouse embryo," Devel., 111:801-811(1991).

Rohwedel et al, "Loss of β1 Integrin Function Results in a Retardation of Myogenic, but an Acceleration of Neuronal, Differentiation of Embryonic Stem Cells in Vitro," Devel. Biol., 201:167-184(1998).

Saga, Yumiko., "Genetic rescue of segmentation defect in MesP2-deficient mice by MesP 1 gene replacement," Mech. of Devel., 75:53-66(1998).

Saito et al., "Bovine embryonic stem cell-like cell lines cultured over several passages," Roux's Arch. Dev. Biol., 201:134-141(1992).

Sims et al., "Interleukin 1 Signaling Occurs Exclusively Via the Type I Receptor," Proc. Natl. Acad. Sci. USA, 90:6155-6159(1993).

Smith et al., "Buffalo Rat Liver Cells Produce a Diffusible Activity Which Inhibits the Differentiation of Murine Embryonal Carcinoma and Embryonic Stem Cells," Devel. Biol., 121:1-9(1987).

Smith et al., "Influence of Nuclear and Cytoplasmic Activity on the Development in Vivo of Sheep Embryos after Nuclear Transplantation," Biol. Reprod., 40:1027-1035(1989).

Soudais et al., "Targeted mutagenesis of the transcription factor GATA-4 gene in mouse embryonic stem cells disrupts visceral endoderm differentiation in vitro," Development, 121:3877-3888(1995).

Stein et al., "Stage-Dependent Redistributions of Acetylated Histones in Nuclei of the Early Preimplantation Mouse Embryo," Molecular Reproduction and Development, 47:421-429(1997).

Stice et al., "Cloning: New Breakthroughs Leading to Commercial Opportunities," Theriogenology, 49:129-138(1998).

Stice et al., "Pluripotent Bovine Embryonic Cell Lines Direct Embryonic Development Following Nuclear Transfer," Biol. Reprod., 54:100-110(1996).

Tada et al., "Embryonic Germ Cells Induce Epigenetic Reprogramming of Somatic Nucleus in Hybrid Cells," EMBO J., 16(21):6510-20(1997).

Thomson et al., "Embryonic Stem Cell Lines Derived from Human Blastocycsts," 282(5391):(1998).

Thomson et al., "Isolation of a primate embryonic stem cell line," Proc. Natl. Acad. Sci., USA, 92:7844-7848(1995).

Urbani et al., "Dissociation of Nuclear and Cytoplasmic Cell Cycle Progression by Drugs Employed in Cell Synchronization," Experimental Cell Research, 219:159-168(1995).

Van Stekelenburg-Hamers et al., "Isolation and Characterization of Permanent Cell Lines From Inner Cell Mass Cells of Bovine Blastocysts," Molecular Reprod. and Devel., 40:444-454(1995).

Wade, "Researchers Claim Embryonic Cell Mix of Human and Cow," The New York Times National, A1, Nov. 12, 1998.

Weiss, "A Cloning Claim's Controversies," Washington Post, A3, Nov. 13, 1998.

Weiss, "Can Scientists Bypass Stem Cells' Moral Minefield?," The Washington Post, A3, Dec. 14, 1998.

Westphal et al., "A Signaling Complex of $Ca^{2+}$[SUP 2+]Calmodulin-Dependent Protein Kinase IV and Protein Phosphatase 2A," Science, 280:1258(1998).

Wilmut, I., and Schnieke, A.E., "Viable offspring derived from fetal and adult mammalian cells," Nature, 385(6619):810-813(1997).

Wolfe et al., "Embryos Produced by the Transfer of Caprine Nuclei to Enucleated Bovine Oocytes are Capable of Cleavage but do not Develop to Blastocysts," Biol. of Reprod. Suppl., (July 24, 1994).

Wolfe et al., "Methods in Bovine Nuclear Transfer," Theriogenology, 37(1):5-15(1992).

Wolfe et al., Preimplantation Development of Embryos Produced by Intergeneric Nuclear Transplantation, Theriogenology, 33(1):350-351(1990).

Yamane, "Primary cultures of various differentiated human cells and their transfer," Gan Tokagaku Ryoho, 14:211-219(1987).

Yang et al., "Nuclear Totipotency of Cultured Rabbit Morulae to Support Full-Term Development Following Nuclear Transfer," Biol. of Reprod., 47:636-643(1992).

Yoshida et al, "Trichostatin A and trapoxin: novel chemical probes for the role of histone acetylation in chromatin structure and function," BioEssays, 17(5):423-430(1995).

Yoshimoto et al., "Astrocytes Retrovirally Transduced with BDNF Elicit Behavioral Improvement in a Rat Model of Parkinson's Disease," Brain Research, 692:25-36(1995).

* cited by examiner

US 7,696,404 B2

EMBRYONIC OR STEM-LIKE CELL LINES PRODUCED BY CROSS SPECIES NUCLEAR TRANSPLANTATION AND METHODS FOR ENHANCING EMBRYONIC DEVELOPMENT BY GENETIC ALTERATION OF DONOR CELLS OR BY TISSUE CULTURE CONDITIONS

CROSS-REFERENCE TO RELATED APPLICATIONS

This application is a continuation-in-part of application Ser. No. 09/467,076 filed Dec. 20, 1999, which is a continuation-in-part of application Ser. No. 09/395,368, filed Sep. 14, 1999, which is a continuation-in-part of application Ser. No. 09/260,468, filed Mar. 2, 1999, which is a continuation-in-part of application Ser. No. 09/032,945, filed Mar. 2, 1998, which is a continuation-in-part of application Ser. No. 08/699,040, filed Aug. 19, 1996, each of which is incorporated by reference in its entirety herein. Application Ser. No. 09/467,076 filed Dec. 20, 1999, also claims priority under 35 U.S.C. §119 to PCT/US99/04608, filed on Mar. 2, 1999, which is incorporated by reference in its entirety herein. This application is also a continuation-in-part of application Ser. No. 09/685,061, filed Oct. 6, 2000, which is a continuation-in-part of application Ser. No. 09/260,468, filed Mar. 2, 1999, and which is incorporated by reference in its entirety herein. This application is also a continuation-in-part of application Ser. No. 09/874,040, filed Jun. 6, 2001, which is a continuation-in-part of application Ser. No. 08/699,040, filed Aug. 19, 1996, and which is incorporated by reference in its entirety herein. This application is also a continuation-in-part of application Ser. No. 09/809,018, filed Mar. 16, 2001, which is a continuation-in-part of application Ser. No. 09/032,945, filed Mar. 2, 1998, and which is incorporated by reference in its entirety herein. This application claims priority to provisional application 60/342,358 filed Dec. 27, 2001, and to provisional application 60/357,848, filed Feb. 21, 2002, each of which is incorporated by reference in its entirety herein.

FIELD OF THE INVENTION

The present invention generally relates to the production of embryonic or stem-like cells by the transplantation of cell nuclei derived from animal or human cells into enucleated animal oocytes of a species different from the donor nuclei. The present invention more specifically relates to the production of primate or human embryonic or stem-like cells by transplantation of the nucleus of a primate or human cell into an enucleated animal oocyte, e.g., a primate or ungulate oocyte. In a preferred embodiment the donor cell or nuclei will be human or non-human primate and the recipient cell will be an oocyte from a Lagomorph, e.g., rabbit, hare or a bovine oocyte.

The present invention further relates to the use of the resultant embryonic or stem-like cells, preferably primate or human embryonic or stem-like cells for therapy, for diagnostic applications, for the production of differentiated cells which may also be used for therapy or diagnosis, and for the production of transgenic embryonic or transgenic differentiated cells, cell lines, tissues and organs. Also, the embryonic or stem-like cells obtained according to the present invention may themselves be used as nuclear donors in nuclear transplantation or nuclear transfer methods for the production of chimeras or clones, preferably transgenic cloned or chimeric animals.

BACKGROUND OF THE INVENTION

Methods for deriving embryonic stem (ES) cell lines in vitro from early pre-implantation mouse embryos are well known. (See, e.g., Evans et al., *Nature*, 29:154-156 (1981); Martin, *Proc. Natl. Acad. Sci., USA*, 78:7634-7638 (1981)). ES cells can be passaged in an undifferentiated state, provided that a feeder layer of fibroblast cells (Evans et al., Id.) or a differentiation inhibiting source (Smith et al., *Dev. Biol.*, 121: 1-9 (1987)) is present.

ES cells have been previously reported to possess numerous applications. For example, it has been reported that ES cells can be used as an in vitro model for differentiation, especially for the study of genes that are involved in the regulation of early development. Mouse ES cells can give rise to germline chimeras when introduced into pre-implantation mouse embryos, thus demonstrating their pluripotency (Bradley et al., *Nature*, 309:255-256 (1984)).

In view of their ability to transfer their genome to the next generation, ES cells have potential utility for germline manipulation of livestock animals by using ES cells with or without a desired genetic modification. Moreover, in the case of livestock animals, e.g., ungulates, nuclei from like pre-implantation livestock embryos support the development of enucleated oocytes to term (Smith et al., *Biol. Reprod.*, 40:1027-1035 (1989); and Keefer et al., *Biol. Reprod.*, 50:935-939 (1994)). This is in contrast to nuclei from mouse embryos, which beyond the eight-cell stage after transfer reportedly do not support the development of enucleated oocytes (Cheong et al, *Biol. Reprod.*, 48:958 (1993)). Therefore, ES cells from livestock animals are highly desirable because they may provide a potential source of totipotent donor nuclei, genetically manipulated or otherwise, for nuclear transfer procedures.

Some research groups have reported the isolation of purportedly pluripotent embryonic cell lines. For example, Notarianni et al., *J. Reprod. Fert. Suppl.*, 43:255-260 (1991), report the establishment of purportedly stable, pluripotent cell lines from pig and sheep blastocysts which exhibit some morphological and growth characteristics similar to that of cells in primary cultures of inner cell masses isolated immunosurgically from sheep blastocysts. (Id.) Also, Notarianni et al., *J. Reprod. Fert. Suppl.*, 41:51-56 (1990) discloses maintenance and differentiation in culture of putative pluripotential embryonic cell lines from pig blastocysts. Further, Gerfen et al., *Anim. Biotech*, 6(1):1-14 (1995) disclose the isolation of embryonic cell lines from porcine blastocysts. These cells are stably maintained in mouse embryonic fibroblast feeder layers without the use of conditioned medium. These cells reportedly differentiate into several different cell types during culture (Gerfen et al., Id.).

Further, Saito et al., *Roux's Arch. Dev. Biol.*, 201:134-141 (1992) report bovine embryonic stem cell-like cell lines cultured which survived passages for three, but were lost after the fourth passage. Still further, Handyside et al., *Roux's Arch. Dev. Biol.*, 196:185-190 (1987) disclose culturing of immunosurgically isolated inner cell masses of sheep embryos under conditions which allow for the isolation of mouse ES cell lines derived from mouse ICMs. Handyside et al. (1987) (Id.), report that under such conditions, the sheep ICMs attach, spread, and develop areas of both ES cell-like and endoderm-like cells, but that after prolonged culture only endoderm-like cells are evident. (Id.)

Recently, Cherny et al., *Theriogenology*, 41:175 (1994) reported purportedly pluripotent bovine primordial germ cell-derived cell lines maintained in long-term culture. These cells, after approximately seven days in culture, produced ES-like colonies that stain positive for alkaline phosphatase (AP), exhibited the ability to form embryoid bodies, and spontaneously differentiated into at least two different cell types. These cells also reportedly expressed mRNA for the transcription factors OCT4, OCT6 and HES1, a pattern of homeobox genes which is believed to be expressed by ES cells exclusively.

Also recently, Campbell et al., *Nature*, 380:64-68 (1996) reported the production of live lambs following nuclear transfer of cultured embryonic disc (ED) cells from day nine ovine embryos cultured under conditions which promote the isolation of ES cell lines in the mouse. The authors concluded based on their results that ED cells from day nine ovine embryos are totipotent by nuclear transfer and that totipotency is maintained in culture.

Van Stekelenburg-Hamers et al., *Mol. Reprod. Dev.*, 40:444-454 (1995), reported the isolation and characterization of purportedly permanent cell lines from inner cell mass cells of bovine blastocysts. The authors isolated and cultured ICMs from 8 or 9 day bovine blastocysts under different conditions to determine which feeder cells and culture media are most efficient in supporting the attachment and outgrowth of bovine ICM cells. They concluded based on their results that the attachment and outgrowth of cultured ICM cells is enhanced by the use of STO (mouse fibroblast) feeder cells instead of bovine uterus epithelial cells) and by the use of charcoal-stripped serum (rather than normal serum) to supplement the culture medium. Van Stekelenburg et al reported, however, that their cell lines resembled epithelial cells more than pluripotent ICM cells. (Id.)

Still further, Smith et al., WO 94/24274, published Oct. 27, 1994, Evans et al, WO 90/03432, published Apr. 5, 1990, and Wheeler et al, WO 94/26889, published Nov. 24, 1994, report the isolation, selection and propagation of animal stem cells which purportedly may be used to obtain transgenic animals. Also, Evans et al., WO 90/03432, published on Apr. 5, 1990, reported the derivation of purportedly pluripotent embryonic stem cells derived from porcine and bovine species which assertedly are useful for the production of transgenic animals. Further, Wheeler et al, WO 94/26884, published Nov. 24, 1994, disclosed embryonic stem cells which are assertedly useful for the manufacture of chimeric and transgenic ungulates. Thus, based on the foregoing, it is evident that many groups have attempted to produce ES cell lines, e.g., because of their potential application in the production of cloned or transgenic embryos and in nuclear transplantation.

The use of ungulate ICM cells for nuclear transplantation has also been reported. For example, Collas et al., *Mol. Reprod. Dev.*, 38:264-267 (1994) disclose nuclear transplantation of bovine ICMs by microinjection of the lysed donor cells into enucleated mature oocytes. The reference disclosed culturing of embryos in vitro for seven days to produce fifteen blastocysts which, upon transferral into bovine recipients, resulted in four pregnancies and two births. Also, Keefer et al., *Biol. Reprod.*, 50:935-939 (1994), disclose the use of bovine ICM cells as donor nuclei in nuclear transfer procedures, to produce blastocysts which, upon transplantation into bovine recipients, resulted in several live offspring. Further, Sims et al., *Proc. Natl. Acad. Sci., USA*, 90:6143-6147 (1993), disclosed the production of calves by transfer of nuclei from short-term in vitro cultured bovine ICM cells into enucleated mature oocytes.

Also, the production of live lambs following nuclear transfer of cultured embryonic disc cells has been reported (Campbell et al., *Nature*, 380:64-68 (1996)). Still further, the use of bovine pluripotent embryonic cells in nuclear transfer and the production of chimeric fetuses have also been reported (Stice et al., *Biol. Reprod.*, 54:100-110 (1996)); Collas et al, *Mol. Reprod. Dev.*, 38:264-267 (1994).

Further, there have been previous attempts to produce cross species NT units (Wolfe et al., *Theriogenology*, 33:350 (1990). Specifically, bovine embryonic cells were fused with bison oocytes to produce some cross species NT units possibly having an inner cell mass. However, embryonic cells, not adult cells were used, as donor nuclei in the nuclear transfer procedure. The dogma has been that embryonic cells are more easily reprogrammed than adult cells. This dates back to earlier NT studies in the frog (review by DiBerardino, *Differentiation*, 17:17-30 (1980)). Also, this study involved very phylogenetically similar animals (cattle nuclei and bison oocytes). By contrast, previously when more diverse species were fused during NT (cattle nuclei into hamster oocytes), no inner cell mass structures were obtained. Further, it has never been previously reported that the inner cell mass cells from NT units could be used to form an ES cell-like colony that could be propagated.

Also, Collas et al (Id.), taught the use of granulosa cells (adult somatic cells) to produce bovine nuclear transfer embryos. However, unlike the present invention, these experiments did not involve cross-species nuclear transfer. Also, unlike the present invention ES-like cell colonies were not obtained.

Recently, U.S. Pat. No. 5,843,780, issued to James A. Thomson on Dec. 1, 1998, assigned to the Wisconsin Alumni Research Foundation, purports to disclose a purified preparation of primate embryonic stem cells that are (i) capable of proliferation in an in vitro culture for over one year; (ii) maintain a karyotype in which all chromosomes characteristic of the primate species are present and not noticeably altered through prolonged culture; (iii) maintains the potential to differentiate into derivatives of endoderm, mesoderm and ectoderm tissues throughout culture; and (iv) will not differentiate when cultured on a fibroblast feeder layer. These cells were reportedly negative for the SSEA-1 marker, positive for the SEA-3 marker, positive for the SSEA-4 marker, express alkaline phosphatase activity, are pluripotent, and have karyotypes which include the presence of all the chromosomes characteristic of the primate species and in which none of the chromosomes are altered. Further, these cells are respectfully positive for the TRA-1-60, and TRA-1-81 markers. The cells purportedly differentiate into endoderm, mesoderm and ectoderm cells when injected into a SCID mouse. Also, purported embryonic stem cell lines derived from human or primate blastocysts are discussed in Thomson et al., *Science* 282:1145-1147 and *Proc. Natl. Acad. Sci., USA* 92:7844-7848 (1995).

Thus, Thomson discloses what purportedly are non-human primate and human embryonic or stem-like cells and methods for their production. However, there still exists a significant need for methods for producing human embryonic or stem-like cells that are autologous to an intended transplant recipient given their significant therapeutic and diagnostic potential.

In this regard, numerous human diseases have been identified which may be treated by cell transplantation. For example, Parkinson's disease is caused by degeneration of dopaminergic neurons in the substantial nigra. Standard treatment for Parkinson's involves administration of L-DOPA, which temporarily ameliorates the loss of dopamine, but causes severe side effects and ultimately does not reverse the progress of the disease. A different approach to treating Parkinson's, which promises to have broad applicability to treatment of many brain diseases and central nervous system injury, involves transplantation of cells or tissues from fetal or neonatal animals into the adult brain. Fetal neurons from a variety of brain regions can be incorporated into the adult brain. Such grafts have been shown to alleviate experimentally induced behavioral deficits, including complex cognitive functions, in laboratory animals. Initial test results from human clinical trials have also been promising. However, supplies of human fetal cells or tissue obtained from miscarriages is very limited. Moreover, obtaining cells or tissues from aborted fetuses is highly controversial.

There is currently no available procedure for producing "fetal-like" cells from the patient. Further, allograft tissue is not readily available and both allograft and xenograft tissue are subject to graft rejection. Moreover, in some cases, it would be beneficial to make genetic modifications in cells or tissues before transplantation. However, many cells or tissues wherein such modification would be desirable do not divide well in culture and most types of genetic transformation require rapidly dividing cells.

There is therefore a clear need in the art for a supply of human embryonic or stem-like undifferentiated cells for use in transplants and cell and gene therapies.

OBJECTS OF THE INVENTION

It is an object of the invention to provide novel and improved methods for producing embryonic or stem-like cells.

It is a more specific object of the invention to provide a novel method for producing embryonic or stem-like cells which involves transplantation of the nucleus of a vertebrate cell, e.g., a mammal, reptile, amphibian or avian into a suitable recipient cell, e.g., an oocyte of a different species.

It is more specific object of the invention to provide a novel method for producing non-human primate or human embryonic or stem-like cells which involves transplantation of the nucleus of a non-human primate or human cell into an a recipient cell, e.g., an animal or human oocyte, e.g., an ungulate, human or primate enucleated oocyte or a Lagomorph oocyte.

It is another object of the invention to enhance the efficacy of cross-species nuclear transfer by incorporating mitochondrial DNA derived from the same species (preferably same donor) as the donor cell into the oocyte of a different species that is used for nuclear transfer, before or after enucleation, or into the nuclear transfer unit (after the donor cell has been introduced). Preferably, the donor cell or nucleus will be a human or non-human primate cell or nucleus and the recipient cell will be an oocyte, e.g., or ungulate or Lagomorph.

It is still another object of the invention to enhance the efficacy of cross-species nuclear transfer by fusing an enucleated somatic cell (e.g., an enucleated human somatic cell) (karyoplast) with an activated or non-activated, enucleated or non-enucleated oocyte of a different species, e.g., bovine, or by fusion with an activated or unactivated cross-species NT unit which may be cleaved or uncleaved.

It is another object of the invention to provide a novel method for producing lineage-defective non-human primate or human embryonic or stem-like cells which involves transplantation of the nucleus of a non-human primate or human cell, e.g., a human adult cell into an enucleated non-human primate or human oocyte, wherein such cell has been genetically engineered to be incapable of differentiation into a specific cell lineage or has been modified such that the cells are "mortal", and thereby do not give rise to a viable offspring, e.g., by engineering expression of anti-sense or ribozyme telomerase gene.

It is still another object of the invention to enhance efficiency of nuclear transfer and specifically to enhance the development of pre-implantation embryos produced by nuclear transfer by genetically engineering donor somatic cells used for nuclear transfer to provide for the expression of genes that enhance embryonic development, e.g., genes of the MHC I family, and in particular Ped genes such as Q7 and/or Q9.

It is another object of the invention to enhance the production of nuclear transfer embryos, e.g., cross-species nuclear transfer embryos, by the introduction of transgenes before or after nuclear transfer that provide for the expression of an antisense DNA encoding a cell death gene such as BAX, Apaf-1, or caspase, or a portion thereof, or demethylase.

It is yet another object of the invention to enhance the production of nuclear transfer embryos by IVP and more specifically nuclear transfer embryos by genetically altering the donor cell used for nuclear transfer such that it is resistant to apoptosis, e.g., by introduction of a DNA construct that provides for the expression of genes that inhibit apoptosis, e.g., Bcl-2 or Bcl-2 family members and/or by the expression of antisense ribozymes specific to genes that induce apoptosis during early embryonic development.

It is still another object of the invention to improve the efficacy of nuclear transfer by improved selection of donor cells of a specific cell cycle stage, e.g., G1 phase, by genetically engineering donor cells such that they express a DNA construct encoding a particular cyclin linked to a detectable marker, e.g., one that encodes a visualizable (e.g., fluorescent tag) marker protein.

It is also an object of the invention to enhance the development of in vitro produced embryos, by culturing such embryos in the presence of one or more protease inhibitors, preferably one or more caspase inhibitors, thereby inhibiting apoptosis.

It is another object of the invention to provide embryonic or stem-like cells produced by transplantation of nucleus of an animal or human cell into an enucleated oocyte of a different species.

It is a more specific object of the invention to provide primate or human embryonic or stem-like cells produced by transplantation of the nucleus of a primate or human cell into an enucleated animal oocyte, e.g., a human, primate or ungulate enucleated oocyte.

It is another object of the invention to use such embryonic or stem-like cells for therapy or diagnosis.

It is a specific object of the invention to use such primate or human embryonic or stem-like cells for treatment or diagnosis of any disease wherein cell, tissue or organ transplantation is therapeutically or diagnostically beneficial.

It is another specific object of the invention to use the embryonic or stem-like cells produced according to the invention for the production of differentiated cells, tissues or organs. In a preferred embodiment these cells will be obtained by fusion or implantation of a human cell or nucleus into a recipient oocyte, e.g., an ungulate (bovine etc.) or a lagomorph, e.g., a rabbit, hare or pika.

It is a more specific object of the invention to use the primate or human embryonic or stem-like cells produced according to the invention for the production of differentiated human cells, tissues or organs.

It is another specific object of the invention to use the embryonic or stem-like cells produced according to the invention for the production of genetically engineered embryonic or stem-like cells, which cells may be used to produce genetically engineered or transgenic differentiated human cells, tissues or organs, e.g., having use in gene therapies.

It is another specific object of the invention to use the embryonic or stem-like cells produced according to the invention in vitro, e.g. for study of cell differentiation and for assay purposes, e.g. for drug studies.

It is another object of the invention to provide improved methods of transplantation therapy, comprising the usage of isogenic or synegenic cells, tissues or organs produced from the embryonic or stem-like cells produced according to the invention. Such therapies include by way of example treatment of diseases and injuries including Parkinson's, Huntington's, Alzheimer's, ALS, spinal cord injuries, multiple sclerosis, muscular dystrophy, diabetes, liver diseases, heart disease, cartilage replacement, burns, vascular diseases, urinary tract diseases, as well as for the treatment of immune defects, bone marrow transplantation, cancer, among other diseases.

It is another object of the invention to use the transgenic or genetically engineered embryonic or stem-like cells produced according to the invention for gene therapy, in particular for the treatment and/or prevention of the diseases and injuries identified, supra.

It is another object of the invention to use the embryonic or stem-like cells produced according to the invention or transgenic or genetically engineered embryonic or stem-like cells produced according to the invention as nuclear donors for nuclear transplantation.

It is still another object of the invention to use genetically engineered ES cells produced according to the invention for the production of transgenic animals, e.g., non-human primates, rodents, ungulates, etc. Such transgenic animals can be used to produce, e.g., animal models for study of human diseases, or for the production of desired polypeptides, e.g., therapeutics or nutripharmaceuticals.

With the foregoing and other objects, advantages and features of the invention that will become hereinafter apparent, the nature of the invention may be more clearly understood by reference to the following detailed description of the preferred embodiments of the invention and to the appended claims.

BRIEFS DESCRIPTION OF THE FIGURES

DETAILED DESCRIPTION OF THE INVENTION

Figure 1:
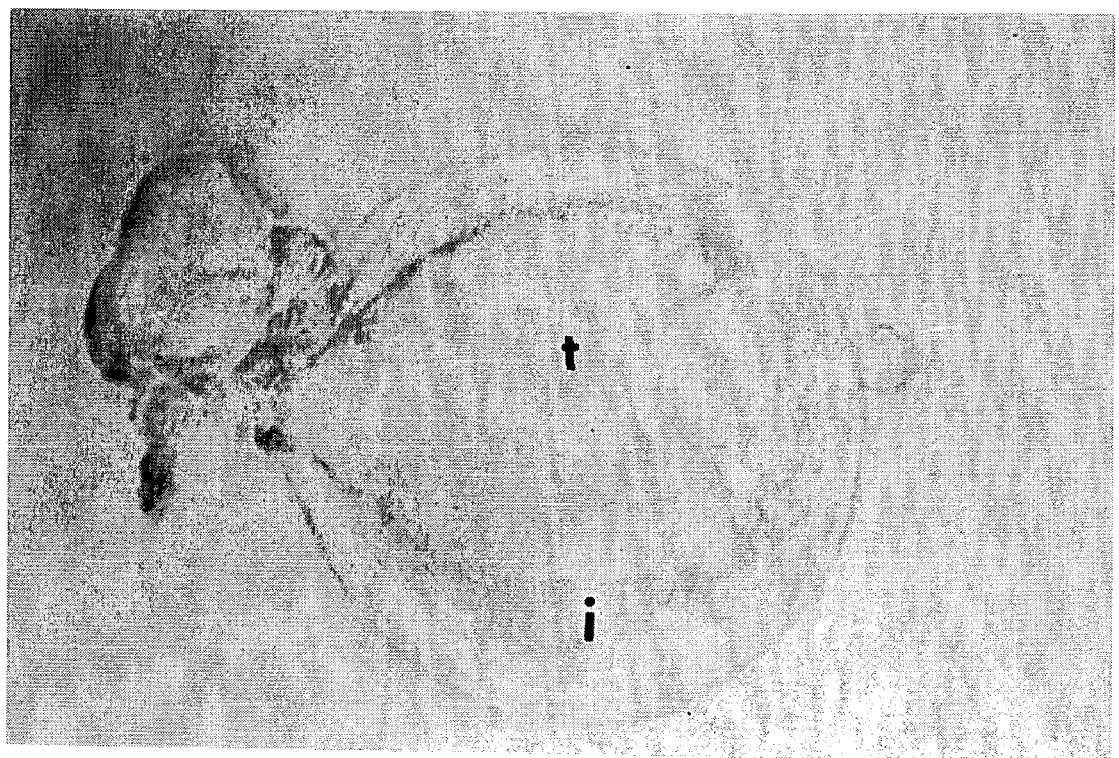
FIG. 1 is a photograph of a nuclear transfer (NT) unit produced by transfer of an adult human cell into an enucleated bovine oocyte.
Figure 2:
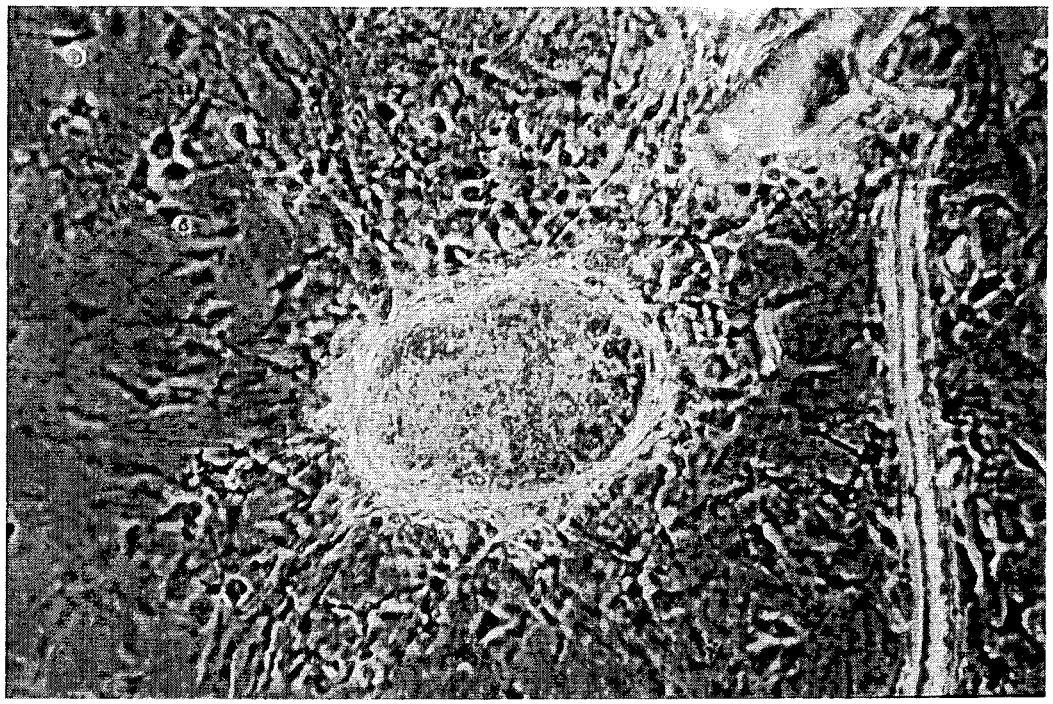
FIGS. 2 to 5 are photographs of embryonic stem-like cells derived from a NT unit such as is depicted in FIG. 1.
Figure 3:
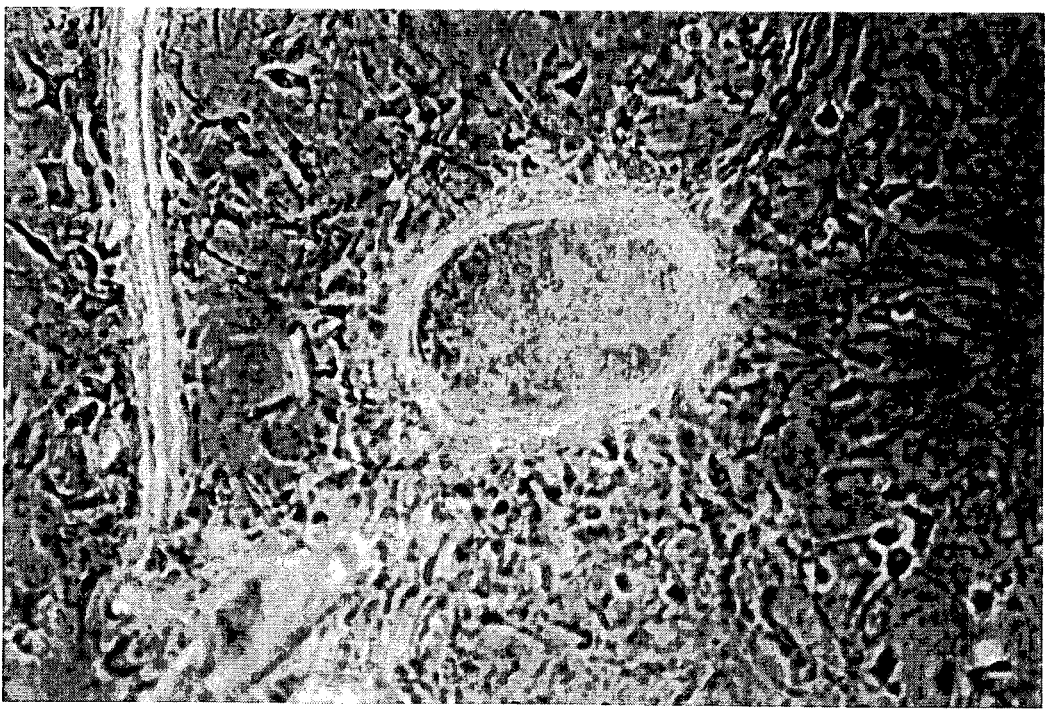
Figure 4:
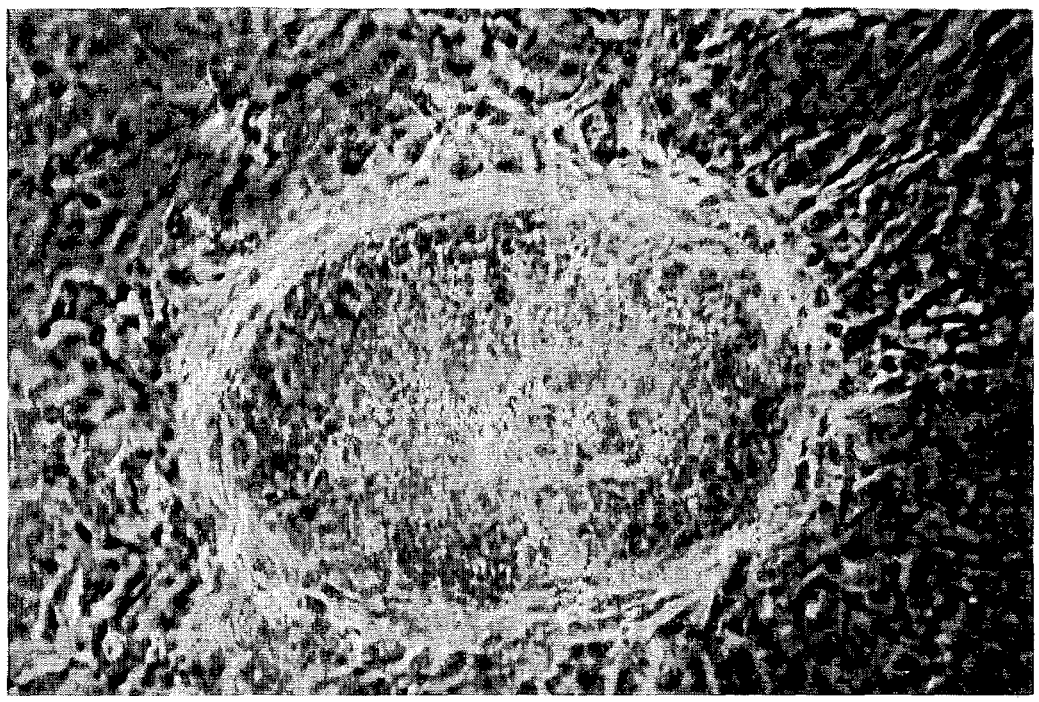
Figure 5:
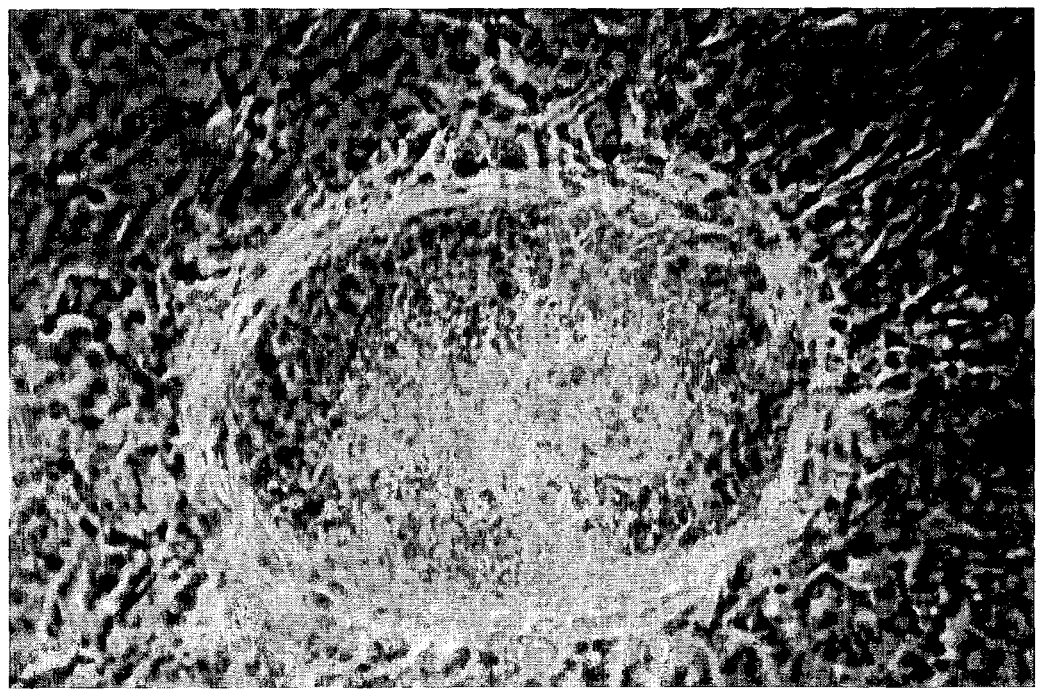

The present invention provides a novel method for producing embryonic or stem-like cells, and more specifically non-human primate or human embryonic or stem-like cells by nuclear transfer or nuclear transplantation. In the subject application, nuclear transfer or nuclear transplantation or NT are used interchangeably.

As discussed supra, the isolation of actual embryonic or stem-like cells by nuclear transfer or nuclear transplantation has never been reported. Rather, previous reported isolation of ES-like cells has been from fertilized embryos. Also, successful nuclear transfer involving cells or DNA of genetically dissimilar species, or more specifically adult cells or DNA of one species (e.g., human) and oocytes of another non-related species has never been reported. Rather, while embryos produced by fusion of cells of closely related species, has been reported, e.g., bovine-goat and bovine-bison, they did not produce ES cells. (Wolfe et al, *Theriogenology*, 33(1):350 (1990).) Also, there has never been reported a method for producing primate or human ES cells derived from a non-fetal tissue source. Rather, the limited human fetal cells and tissues which are currently available must be obtained or derived from spontaneous abortion tissues and from aborted fetuses.

Also, prior to the present invention, no one obtained embryonic or stem-like cells by cross-species nuclear transplantation.

Quite unexpectedly, the present inventors discovered that human embryonic or stem-like cells and cell colonies may be obtained by transplantation of the nucleus of a human cell, e.g., an adult differentiated human cell, into an enucleated animal oocyte, which is used to produce nuclear transfer (NT) units, the cells of which upon culturing give rise to human embryonic or stem-like cells and cell colonies. This result is highly surprising because it is the first demonstration of effective cross-species nuclear transplantation involving the introduction of a differentiated donor cell or nucleus into an enucleated oocyte of a genetically dissimilar species, e.g., the transplantation of cell nuclei from a differentiated animal or human cell, e.g., adult cell, into the enucleated egg of a different animal species, to produce nuclear transfer units containing cells which when cultured under appropriate conditions give rise to embryonic or stem-like cells and cell colonies. In preferred embodiments, the donor cell or nucleus and recipient cell (oocyte) will be of different order organism. For example, in a preferred embodiment the donor cell or nucleus is human or non-human primate and the recipient cell (oocyte) is an ungulate or Lagomorpha oocyte, preferably a rabbit or hare. Examples, thereof, including domesticated rabbits, jack rabbits, hares, cottontails, snowshoe and others. This order includes animals of the genera *lepus, sylvilagus* and *oryctolugus*.

In a preferred embodiment nuclear transfer units produced according to the invention will be allowed to develop into blastocysts or morula stage embryos and these blastocysts, morula stage embryos or portions thereof, e.g., the inner cell mass will be induced to differentiate into desired cell lineages by contacting with different growth factors, hormones and other constituents that induce cell differentiate. Alternatively, differentiation can be effected in vitro by implantation into a suitable surrogate animal.

Preferably, the NT units used to produce ES-like cells will be cultured to a size of at least 2 to 400 cells, preferably 4 to 128 cells, and most preferably to a size of at least about 50 cells.

In the present invention, embryonic or stem-like cells refer to cells produced according to the present invention. The present application refers to such cells as stem-like cells rather than stem cells because of the manner in which they are typically produced, i.e., by cross-species nuclear transfer. While these cells are expected to possess similar differentiation capacity as normal stem cells they may possess some insignificant differences because of the manner they are produced. For example, these stem-like cells may possess the mitochondria of the oocytes used for nuclear transfer, and thus not behave identically to conventional embryonic stem cells.

The present discovery was made based on the observation that nuclear transplantation of the nucleus of an adult human cell, specifically a human epithelial cell obtained from the oral cavity of a human donor, when transferred into an enucleated bovine oocyte, resulted in the formation of nuclear transfer units, the cells of which upon culturing gave rise to human stem-like or embryonic cells and human embryonic or stem-like cell colonies. This result has recently been reproduced by transplantation of keratinocytes from an adult human into an enucleated bovine oocyte with the successful production of a blastocyst and ES cell line. Based thereon, it is hypothesized by the present inventors that bovine oocytes and human oocytes, and likely mammals in general must undergo maturation processes during embryonic development which are sufficiently similar or conserved so as to permit the bovine oocyte to function as an effective substitute or surrogate for a human oocyte. Apparently, oocytes in general comprise factors, likely proteinaceous or nucleic acid in nature, that induce embryonic development under appropriate conditions, and these functions that are the same or very similar in different species. These factors may comprise material RNAs and/or telomerase.

Based on the fact that human cell nuclei can be effectively transplanted into bovine oocytes, it is reasonable to expect that human cells may be transplanted into oocytes of other non-related species, e.g., other ungulates as well as other animals. In particular, other ungulate oocytes should be suitable, e.g. pigs, sheep, horses, goats, etc. Also, oocytes from other sources should be suitable, e.g. oocytes derived from other primates, amphibians, rodents, rabbits, guinea pigs, etc. Further, using similar methods, it should be possible to transfer human cells or cell nuclei into human oocytes and use the resultant blastocysts to produce human ES cells.

In fact, as disclosed in an exemplified protocol infra in the examples, the present inventor have produced blastocysts by fusion of a human donor cell and a rabbit oocyte which has been enucleated to remove its endogenous nucleus.

Therefore, in its broadest embodiment, the present invention involves the transplantation of human cell nucleus or animal or human cell into an oocyte (preferably enucleated) of an animal species different from the donor nuclei, by injection or fusion, to produce an NT unit containing cells which may be used to obtain embryonic or stem-like cells and/or cell cultures. Enucleation (removal of endogenous oocyte nucleus) may be effected before or after nuclear transfer. For example, the invention may involve the transplantation of an ungulate cell nucleus or ungulate cell into an enucleated oocyte of another species, e.g., another ungulate or non-ungulate, by injection or fusion, which cells and/or nuclei are combined to produce NT units and which are cultured under conditions suitable to obtain multicellular NT units, preferably comprising at least about 2 to 400 cells, more preferably 4 to 128 cells, and most preferably at least about 50 cells. The cells of such NT units may be used to produce embryonic or stem-like cells or cell colonies upon culturing.

However, the preferred embodiment of the invention comprises the production of non-human primate or human embryonic or stem-like cells by transplantation of the nucleus of a donor human cell or a human cell into an enucleated human, primate, or non-primate animal oocyte, e.g., an ungulate oocyte, and in a preferred embodiment a bovine enucleated oocyte or a lagomorpha oocyte, e.g., rabbit, hare or pika.

In general, the embryonic or stem-like cells will be produced by a nuclear transfer process comprising the following steps:

(i) obtaining desired human or animal cells to be used as a source of donor nuclei (which may be genetically altered);
(ii) obtaining oocytes from a suitable source, e.g. a mammal and most preferably a primate or an ungulate source, e.g. bovine,
(iii) enucleating said oocytes by removal of endogenous nucleus;
(iv) transferring the human or animal cell or nucleus into the enucleated oocyte of an animal species different than the donor cell or nuclei, e.g., by fusion or injection, wherein steps (iii) and (iv) may be effected in either order;
(v) culturing the resultant NT product or NT unit to produce multiple cell structures (embryoid structures having a discernible inner cell mass); and
(vi) culturing cells obtained from said embryos to obtain embryonic or stem-like cells and stem-like cell colonies.

Nuclear transfer techniques or nuclear transplantation techniques are known in the literature and are described in many of the references cited in the Background of the Invention. See, in particular, Campbell et al, *Theriogenology*, 43:181 (1995); Collas et al, *Mol. Report Dev.*, 38:264-267 (1994); Keefer et al, *Biol. Reprod.*, 50:935-939 (1994); Sims et al, *Proc. Natl. Acad. Sci., USA*, 90:6143-6147 (1993); WO 94/26884; WO 94/24274, and WO 90/03432, which are incorporated by reference in their entirety herein. Also, U.S. Pat. Nos. 4,944,384 and 5,057,420 describe procedures for bovine nuclear transplantation. See, also Cibelli et al, *Science, Vol.* 280:1256-1258 (1998).

Human or animal cells, preferably mammalian cells, may be obtained and cultured by well known methods. Human and animal cells useful in the present invention include, by way of example, epithelial, neural cells, epidermal cells, keratinocytes, hematopoietic cells, melanocytes, chondrocytes, lymphocytes (B and T lymphocytes), other immune cells, erythrocytes, macrophages, melanocytes, monocytes, mononuclear cells, fibroblasts, cardiac muscle cells, cumulus cells and other muscle cells, etc. Moreover, the human cells used for nuclear transfer may be obtained from different organs, e.g., skin, lung, pancreas, liver, stomach, intestine, heart, reproductive organs, bladder, kidney, urethra and other urinary organs, etc. These are just examples of suitable donor cells. Suitable donor cells, i.e., cells useful in the subject invention, may be obtained from any cell or organ of the body. This includes all somatic or germ cells e.g., primordial germ cells, sperm cells. Preferably, the donor cells or nucleus can actively dividing, i.e., non-quiescent, cells as this has been reported to enhance cloning efficacy. Such cells include those in the G1, G2 S or M cell phase. Alternatively, quiescent cells may be used. Also preferably, such donor cells will be in the G1 cell cycle.

The resultant blastocysts may be used to obtain embryonic stem cell lines according to the culturing methods reported by Thomson et al., *Science*, 282:1145-1147 (1998) and Thomson et al., *Proc. Natl. Acad. Sci., USA*, 92:7544-7848 (1995), incorporated by reference in their entirety herein.

In one Example disclosed infra, the cells used as donors for nuclear transfer were epithelial cells derived from the oral cavity of a human donor and adult human keratinocytes. However, as discussed, the disclosed method is applicable to other human cells or nuclei. Moreover, the cell nuclei may be obtained from both human somatic and germ cells. In the second example, the donor cell is a human cell, somatic cell and the recipient cell is an enucleated rabbit oocyte. The fact that both rabbit oocytes and bovine oocytes upon fusion with a human cell yield nuclear transfer units that clear and give rise to which appears to be a cell cloning an exhibiting ES-like appearance supports Applicants belief that the application of a variety of different species, very distinct from primate can be used to reprogram the nuclei of a human cell. It is anticipated especially that other mammalian cells will be suitable, under appropriate culture and activation conditions.

It is also possible to arrest donor cells at mitosis before nuclear transfer, using a suitable technique known in the art. Methods for stopping the cell cycle at various stages have been thoroughly reviewed in U.S. Pat. No. 5,262,409, which is herein incorporated by reference. In particular, while cycloheximide has been reported to have an inhibitory effect on mitosis (Bowen and Wilson (1955) *J. Heredity*, 45:3-9), it may also be employed for improved activation of mature bovine follicular oocytes when combined with electric pulse treatment (Yang et al. (1992) *Biol. Reprod.*, 42 (Suppl. 1): 117).

Zygote gene activation is associated with hyperacetylation of Histone H4. Trichostatin-A has been shown to inhibit histone deacetylase in a reversible manner (Adenot et al. Differential H4 acetylation of paternal and maternal chromatin precedes DNA replication and differential transcriptional activity in pronuclei of 1-cell mouse embryos. *Development* (November 1997) 124(22): 4615-4625; Yoshida et al. Trichostatin A and trapoxin: novel chemical probes for the role of histone acetylation in chromatin structure and function. *Bioessays* (May, 1995) 17(5): 423430), as have other compounds. For instance, butyrate is also believed to cause hyperacetylations of histones by inhibiting histone deacetylase. Generally, butyrate appears to modify gene expression and in almost all cases its addition to cells in culture appears to arrest cell growth. Use of butyrate in this regard is described in U.S. Pat. No. 5,681,718, which is herein incorporated by reference. Thus, donor cells may be exposed to Trichostatin-A or another appropriate deacetylase inhibitor prior to fusion, or such a compound may be added to the culture media prior to genome activation.

Additionally, demethylation of DNA is thought to be a requirement for proper access of transcription factors to DNA regulatory sequences. Global demethylation of DNA from the eight-cell stage to the blastocyst stage in pre-implantation embryos has previously been described (Stein et al., *Mol. Reprod. & Dev.*, 47(4): 421-429). Also, Jaenisch et al. (1997) have reported that 5-azacytidine can be used to reduce the level of DNA methylation in cells, potentially leading to increased access of transcription factors to DNA regulatory sequences. Accordingly, donor cells may be exposed to 5-azacytidine (5-Aza) previous to fusion, or 5-Aza may be added to the culture medium from the 8 cell stage to blastocyst. Alternatively, other known methods for effecting DNA demethylation may be used.

The oocytes used for nuclear transfer may be obtained from animals including mammals, avians, reptiles and amphibians. Suitable mammalian sources for oocytes include sheep, bovines, ovines, pigs, horses, rabbits, goats, guinea pigs, mice, hamsters, rats, primates, humans, etc. In the preferred embodiments, the oocytes will be obtained from primates, lagomorphs or ungulates, e.g., a bovine or rabbits.

Methods for isolation of oocytes are well known in the art. Essentially, this will comprise isolating oocytes from the ovaries or reproductive tract of a mammal or amphibian, e.g., a bovine. A readily available source of bovine oocytes is slaughterhouse materials. Rabbit oocytes are also readily available. As noted, enucleation may be effected before or after nuclear or cell transplantation.

For the successful use of techniques such as genetic engineering, nuclear transfer and cloning, oocytes are preferably matured in vitro before these cells may be used as recipient cells for nuclear transfer, and before they can be fertilized by the sperm cell to develop into an embryo. This process generally requires collecting immature (prophase I) oocytes from animal ovaries, e.g., bovine ovaries obtained at a slaughterhouse and maturing the oocytes in a maturation medium prior to fertilization or enucleation until the oocyte attains the metaphase II stage, which in the case of bovine oocytes generally occurs about 18-24 hours post-aspiration. For purposes of the present invention, this period of time is known as the "maturation period." As used herein for calculation of time periods, "aspiration" refers to aspiration of the immature oocyte from ovarian follicles.

Additionally, metaphase II stage oocytes, which have been matured in vivo have been successfully used in nuclear transfer techniques. Essentially, mature metaphase II oocytes are collected surgically from either non-superovulated or superovulated cows or heifers 35 to 48 hours past the onset of estrus or past the injection of human chorionic gonadotropin (hCG) or similar hormone. Alternatively, metaphase I oocytes may be utilized.

The stage of maturation of the oocyte at enucleation and nuclear transfer has been reported to be significant to the success of NT methods. (See e.g., Prather et al., *Differentiation*, 48, 1-8, 1991). In general, previous successful mammalian embryo cloning practices used metaphase 11 stage oocyte as the recipient oocyte because at this stage it is believed that the oocyte can be or is sufficiently "activated" to treat the introduced nucleus as it does a fertilizing sperm. In domestic animals, and especially cattle, the oocyte activation period generally ranges from about 16-52 hours, preferably about 28-42 hours post-aspiration.

For example, immature oocytes may be washed in HEPES buffered hamster embryo culture medium (HECM) as described in Seshagine et al., *Biol. Reprod.*, 40, 544-606, 1989, and then placed into drops of maturation medium consisting of 50 microliters of tissue culture medium (TCM) 199 containing 10% fetal calf serum which contains appropriate gonadotropins such as luteinizing hormone (LH) and follicle stimulating hormone (FSH), and estradiol under a layer of lightweight paraffin or silicon at 39° C.

After a fixed time maturation period, which typically will range from about 10 to 40 hours, and preferably about 16-18 hours, the oocytes will typically be enucleated. Prior to enucleation the oocytes will preferably be removed and placed in HECM containing I milligram per milliliter of hyaluronidase prior to removal of cumulus cells. This may be effected by repeated pipetting through very fine bore pipettes or by vortexing briefly. The stripped oocytes are then screened for polar bodies, and the selected metaphase II oocytes, as determined by the presence of polar bodies, are then used for nuclear transfer. Enucleation follows. As noted above, enucleation may be effected before or after introduction of donor cell or nucleus because the donor nucleus is readily discernible from endogenous nucleus.

Enucleation may be effected by known methods, such as described in U.S. Pat. No. 4,994,384 which is incorporated by reference herein. For example, metaphase II oocytes are either placed in HECM, optionally containing 7.5 micrograms per milliliter cytochalasin B, for immediate enucleation, or may be placed in a suitable medium, for example CR1aa, plus 10% estrus cow serum, and then enucleated later, preferably not more than 24 hours later, and more preferably 16-18 hours later.

Enucleation may be accomplished microsurgically using a micropipette to remove the polar body and the adjacent cytoplasm. The oocytes may then be screened to identify those of which have been successfully enucleated. This screening may be effected by staining the oocytes with 1 microgram per milliliter 33342 Hoechst dye in HECM, and then viewing the oocytes under ultraviolet irradiation for less than 10 seconds. The oocytes that have been successfully enucleated can then be placed in a suitable culture medium.

In the present invention, the recipient oocytes will typically be enucleated at a time ranging from about 10 hours to about 40 hours after the initiation of in vitro maturation, more preferably from about 16 hours to about 24 hours after initiation of in vitro maturation, and most preferably about 16-18 hours after initiation of in vitro maturation. Enucleation may be effected before, simultaneous or after nuclear transfer. Also, enucleation may be effected before, after or simultaneous to activation.

A single animal or human cell or nucleus derived therefrom which is typically heterologous to the enucleated oocyte will then be transferred into the perivitelline space of the oocyte, typically enucleated, used to produce the NT unit. However, removal of endogenous nucleus may alternatively be effected after nuclear transfer. The animal or human cell or nucleus and the enucleated oocyte will be used to produce NT units according to methods known in the art. For example, the cells may be fused by electrofusion. Electrofusion is accomplished by providing a pulse of electricity that is sufficient to cause a transient break down of the plasma membrane. This breakdown of the plasma membrane is very short because the membrane reforms rapidly. Essentially, if two adjacent membranes are induced to break down, upon reformation the lipid bilayers intermingle and small channels will open between the two cells. Due to the thermodynamic instability of such a small opening, it enlarges until the two cells become one. Reference is made to U.S. Pat. No. 4,997,384, by Prather et al., (incorporated by reference in its entirety herein) for a further discussion of this process. A variety of electrofusion media can be used including e.g., sucrose, mannitol, sorbitol and phosphate buffered solution. Fusion can also be accomplished using Sendai virus as a fusogenic agent (Graham, *Wister Inot. Symp. Monogr.*, Sep. 19, 1969).

Also, in some cases (e.g. with small donor nuclei) it may be preferable to inject the nucleus directly into the oocyte rather than using electroporation fusion. Such techniques are disclosed in Collas and Barnes, *Mol. Reprod. Dev.*, 38:264-267 (1994), and incorporated by reference in its entirety herein.

Preferably, the human or animal cell and oocyte are electrofused in a 500 μm chamber by application of an electrical pulse of 90-120V for about 15 μsec, about 24 hours after initiation of oocyte maturation. After fusion, the resultant fused NT units are preferably placed in a suitable medium until activation, e.g., one identified infra. Typically activation will be effected shortly thereafter, typically less than 24 hours later, and preferably about 4-9 hours later. However, it is also possible to activate the recipient oocyte before or proximate (simultaneous) to nuclear transfer, which may or may not be enucleated. For example, activation may be effected from about twelve hours prior to nuclear transfer to about twenty-four hours after nuclear transfer. More typically, activation is effected simultaneous or shortly after nuclear transfer, e.g., about four to nine hours later.

The NT unit may be activated by known methods. Such methods include, e.g., culturing the NT unit at sub-physiological temperature, in essence by applying a cold, or actually cool temperature shock to the NT unit. This may be most conveniently done by culturing the NT unit at room temperature, which is cold relative to the physiological temperature conditions to which embryos are normally exposed.

Alternatively, activation may be achieved by application of known activation agents. For example, penetration of oocytes by sperm during fertilization has been shown to activate prefusion oocytes to yield greater numbers of viable pregnancies and multiple genetically identical calves after nuclear transfer. Also, treatments such as electrical and chemical shock or cycloheximide treatment may also be used to activate NT embryos after fusion. Suitable oocyte activation methods are the subject of U.S. Pat. No. 5,496,720, to Susko-Parrish et al., which is herein incorporated by reference.

For example, oocyte activation may be effected by simultaneously or sequentially:
(i) increasing levels of divalent cations in the oocyte, and
(ii) reducing phosphorylation of cellular proteins in the oocyte.

This will generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators.

Phosphorylation may be reduced by known methods, e.g., by the addition of kinase inhibitors, e.g., serine-threonine kinase inhibitors, such as 6-dimethylamino-purine, staurosporine, 2-aminopurine, and sphingosine.

Alternatively, phosphorylation of cellular proteins may be inhibited by introduction of a phosphatase into the oocyte, e.g., phosphatase 2A and phosphatase 2B.

Specific examples of activation methods are listed below.
1. Activation by Ionomycin and DMAP
   1—Place oocytes in Ionomycin (5 μM) with 2 mM of DMAP for 4 minutes;
   2—Move the oocytes into culture media with 2 mM of DMAP for 4 hours;
   3—Rinse four times and place in culture.
2. Activation by Ionomycin DMAP and Roscovitin
   1—Place oocytes in Ionomycin (5 μM) with 2 mM of DMAP for four minutes;
   2—Move the oocytes into culture media with 2 mM of DMAP and 200 microM of Roscovitin for three hours;
   3—Rinse four times and place in culture.
3. Activation by exposure to Ionomycin followed by cytochalasin and cycloheximide.
   1—Place oocytes in Ionomycin (5 microM) for four minutes;
   2—Move oocytes to culture media containing 5 μg/ml of cytochalasin B and 5 μg/ml of cycloheximide for five hours;
   3—Rinse four times and place in culture.
4. Activation by electrical pulses
   1—Place eggs in mannitol media containing 100 μM $CaCL_2$;
   2—Deliver three pulses of 1.0 $kVcm^{-1}$ for 20 μsec, each pulse 22 minutes apart;
   3—Move oocytes to culture media containing 5 μg/ml of cytochalasin B for three hours.
5. Activation by exposure with ethanol followed by cytochalasin and cycloheximide
   1—Place oocytes in 7% ethanol for one minute;
   2—Move oocytes to culture media containing 5 μg/ml of cytochalasin B and 5 μg/ml of cycloheximide for five hours;
   3—Rinse four times and place in culture.
6. Activation by microinjection of adenophostine
   1—Inject oocytes with 10 to 12 picoliters of a solution containing 10 μM of adenophostine;
   2—Put oocytes in culture.
7. Activation by microinjection of sperm factor
   1—Inject oocytes with 10 to 12 picoliters of sperm factor isolated, e.g., from primates, pigs, bovine, sheep, goats, horses, mice, rats, rabbits or hamsters;
   2—Put eggs in culture.

8. Activation by microinjection of recombinant sperm factor.
9. Activation by Exposure to DMAP followed by Cycloheximide and Cytochalasin B Place oocytes or NT units, typically about 22 to 28 hours post maturation in about 2 mM DMAP for about one hour, followed by incubation for about two to twelve hours, preferably about eight hours, in 5 µg/ml of cytochalasin B and 20 µg/ml cycloheximide.

The above activation protocols are exemplary of protocols used for nuclear transfer-procedures, e.g., those including the use of primate or human donor cells or oocytes. However, the above activation protocols may be used when either or both the donor cell and nucleus is of ungulate origin, e.g., a sheep, buffalo, horse, goat, bovine, pig and/or wherein the oocyte is of ungulate origin, e.g., sheet, pig, buffalo, horse, goat, bovine, etc., as well as for other species, e.g., Lagomorphs such as rabbits and hares.

As noted, activation may be effected before, simultaneous, or after nuclear transfer. In general, activation will be effected about 40 hours prior to nuclear transfer and fusion to about 40 hours after nuclear transfer and fusion, more preferably about 24 hours before to about 24 hours after nuclear transfer and fusion, and most preferably from about 4 to 9 hours before nuclear transfer and fusion to about 4 to 9 hours after nuclear transfer and fusion. Activation is preferably effected after or proximate to in vitro or in vivo maturation of the oocyte, e.g., approximately simultaneous or within about 40 hours of maturation, more preferably within about 24 hours of maturation.

Activated NT units may be cultured in a suitable in vitro culture medium until the generation of embryonic or stem-like cells and cell colonies. Culture media suitable for culturing and maturation of embryos are well known in the art. Examples of known media, which may be used for bovine embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media. One of the most common media used for the collection and maturation of oocytes is TCM-199, and 1 to 20% serum supplement including fetal calf serum, newborn serum, estrual cow serum, lamb serum or steer serum. A preferred maintenance medium includes TCM-199 with Earl salts, 10% fetal calf serum, 0.2 Ma pyruvate and 50 µg/ml gentamicin sulphate. Any of the above may also involve co-culture with a variety of cell types such as granulosa cells, oviduct cells, BRL cells and uterine cells and STO cells.

In particular, human epithelial cells of the endometrium secrete leukemia inhibitory factor (LIF) during the preimplantation and implantation period. Therefore, the addition of LIF to the culture medium could be of importance in enhancing the in vitro development of the reconstructed embryos. The use of LIF for embryonic or stem-like cell cultures has been described in U.S. Pat. No. 5,712,156, which is herein incorporated by reference.

Another maintenance medium is described in U.S. Pat. No. 5,096,822 to Rosenkrans, Jr. et al., which is incorporated herein by reference. This embryo medium, named CR1, contains the nutritional substances necessary to support an embryo. CR1 contains hemicalcium L-lactate in amounts ranging from 1.0 mM to 10 mM, preferably 1.0 mM to 5.0 mM. Hemicalcium L-lactate is L-lactate with a hemicalcium salt incorporated thereon.

Also, suitable culture medium for maintaining human embryonic cells in culture as discussed in Thomson et al., Science, 282:1145-1147 (1998) and Proc. Natl. Acad. Sci., USA, 92:7844-7848 (1995).

Afterward, the cultured NT unit or units are preferably washed and then placed in a suitable media, e.g., CR1aa medium, Ham's F-10, Tissue Culture Media-199 (TCM-199). Tyrodes-Albumin-Lactate-Pyruvate (TALP) Dulbecco's Phosphate Buffered Saline (PBS), Eagle's or Whitten's, preferably containing about 10% FCS. Such culturing will preferably be effected in well plates which contain a suitable confluent feeder layer. Suitable feeder layers include, by way of example, fibroblasts and epithelial cells, e.g., fibroblasts and uterine epithelial cells derived from ungulates, chicken fibroblasts, murine (e.g., mouse or rat) fibroblasts, STO and SI-m220 feeder cell lines, and BRL cells.

In the preferred embodiment, the feeder cells will comprise mouse embryonic fibroblasts. Means for preparation of a suitable fibroblast feeder layer are described in the example which follows and is well within the skill of the ordinary artisan.

In a preferred embodiment the nuclear transfer unit, or blastocysts, morula or inner cell mast or cells derived therefrom, are permitted to differentiate into desired cell lineages by expression to different combinations of growth factors, hormones will be derived from the same species as the donor cell or nucleus.

Also preferably, the growth factors or hormones will be recombinantly produced rather than isolated directly from an animal, to avoid viral contaminants.

The NT units are preferably cultured on a feeder layer until the NT units reach a size suitable for obtaining cells which may be used to produce embryonic stem-like cells or cell colonies. Preferably, these NT units will be cultured until they reach a size of at least about 2 to 400 cells, more preferably about 4 to 128 cells, and most preferably at least about 50 cells. The culturing will be effected under suitable conditions, i.e., about 38.5□C. and 5% $CO_2$, with the culture medium changed in order to optimize growth typically about every 2-5 days, preferably about every 3 days.

In the case of human cell/enucleated bovine oocyte derived NT units, sufficient cells to produce an ES cell colony, typically on the order of about 50 cells, will be obtained about 12 days after initiation of oocyte activation. However, this may vary dependent upon the particular cell used as the nuclear donor, the species of the particular oocyte, and culturing conditions. One skilled in the art can readily ascertain visually when a desired sufficient number of cells has been obtained based on the morphology of the cultured NT units.

In the case of human/human nuclear transfer embryos, or other embryos produced using non-human primate donor or oocyte, it may be advantageous to use culture medium known to be useful for maintaining human and other primate cells in tissue culture. Examples of a culture media suitable for human embryo culture include the medium reported in Jones et al, Human Reprod., 13(1):169-177 (1998), the P1-catalog #99242 medium, and the P-1 catalog #99292 medium, both available from Irvine Scientific, Santa Ana, Calif., and those used by Thomson et al. (1998) and (1995), which references are incorporated by reference in their entirety.

Another preferred medium comprises ACM+uridine+glucose+1000 IU of LIF. As discussed above, the cells used in the present invention will preferably comprise mammalian somatic cells, most preferably cells derived from an actively proliferating (non-quiescent) mammalian cell culture. In an especially preferred embodiment, the donor cell will be genetically modified by the addition, deletion or substitution of a desired DNA sequence. For example, the donor cell, e.g., a keratinocyte or fibroblast, e.g., of human, primate or bovine origin, may be transfected or transformed with a DNA construct that provides for the expression of a desired gene product, e.g., therapeutic polypeptide. Examples thereof include lymphokines, e.g., IGF-II, IGF-II, interferons, colony stimulating factors, connective tissue polypeptides such as collagens, genetic factors, clotting factors, enzymes, enzyme inhibitors, etc.

Also, as discussed above, the donor cells may be modified prior to nuclear transfer, e.g., to effect impaired cell lineage development, enhanced embryonic development and/or inhibition of apoptosis. Examples of desirable modifications are discussed further below.

One aspect of the invention will involve genetic modification of the donor cell, e.g., a human cell, such that it is lineage deficient and therefore when used for nuclear transfer it will be unable to give rise to a viable offspring. This is desirable especially in the context of human nuclear transfer embryos, wherein for ethical reasons, production of a viable embryo may be an unwanted outcome. This can be effected by genetically engineering a human cell such that it is incapable of differentiating into specific cell lineages when used for nuclear transfer. In particular, cells may be genetically modified such that when used as nuclear transfer donors the resultant "embryos" do not contain or substantially lack at least one of mesoderm, endoderm or ectoderm tissue.

This can be accomplished by, e.g., knocking out or impairing the expression of one or more mesoderm, endoderm or ectoderm specific genes. Examples thereof include:

| | |
|---|---|
| Mesoderm: | SRF, MESP-1, HNF-4, beta-I integrin, MSD; |
| Endoderm: | GATA-6, GATA-4; |
| Ectoderm: | RNA helicase A, H beta 58. |

The above list is intended to be exemplary and non-exhaustive of known genes which are involved in the development of mesoderm, endoderm and ectoderm. The generation of mesoderm deficient, endoderm deficient and ectoderm deficient cells and embryos has been previously reported in the literature. See, e.g., Arsenian et al, *EMBO J.*, Vol. 17(2):6289-6299 (1998); Saga Y, *Mech. Dev.*, Vol. 75(1-2):53-66 (1998); Holdener et al, *Development*, Vol. 120(5):1355-1346 (1994); Chen et al, *Genes Dev.* Vol. 8(20):2466-2477 (1994); Rohwedel et al, *Dev. Biol.*, 201(2): 167-189 (1998) (mesoderm); Morrisey et al, *Genes, Dev.*, Vol. 12(22):3579-3590 (1998); Soudais et al, *Development*, Vol. 121(11):3877-3888 (1995) (endoderm); and Lee et al, *Proc. Natl. Acad. Sci. USA*, Vol. 95:(23): 13709-13713 (1998); and Radice et al, *Development*, Vol. 111(3):801-811 (1991) (ectoderm).

In general, a desired somatic cell, e.g., a human keratinocyte, epithelial cell or fibroblast, will be genetically engineered such that one or more genes specific to particular cell lineages are "knocked out" and/or the expression of such genes significantly impaired. This may be effected by known methods, e.g., homologous recombination. A preferred genetic system for effecting "knock-out" of desired genes is disclosed by Capecchi et al, U.S. Pat. Nos. 5,631,153 and 5,464,764, which reports positive-negative selection (PNS) vectors that enable targeted modification of DNA sequences in a desired mammalian genome. Such genetic modification will result in a cell that is incapable of differentiating into a particular cell lineage when used as a nuclear transfer donor.

This genetically modified cell will be used to produce a lineage-defective nuclear transfer embryo, i.e., that does not develop at least one of a functional mesoderm, endoderm or ectoderm. Thereby, the resultant embryos, even if implanted, e.g., into a human uterus, would not give rise to a viable offspring. However, the ES cells that result from such nuclear transfer will still be useful in that they will produce cells of the one or two remaining non-impaired lineage. For example, an ectoderm deficient human nuclear transfer embryo will still give rise to mesoderm and endoderm derived differentiated cells. An ectoderm deficient cell can be produced by deletion and/or impairment of one or both of RNA helicase A or H beta 58 genes.

These lineage deficient donor cells may also be genetically modified to express another desired DNA sequence.

Thus, the genetically modified donor cell will give rise to a lineage-deficient blastocyst which, when plated, will differentiate into at most two of the embryonic germ layers.

Alternatively, the donor cell can be modified such that it is "mortal". This can be achieved by expressing anti-sense or ribozyme telomerase genes. This can be effected by known genetic methods that will provide for expression of antisense DNA or ribozymes, or by gene knockout. These "mortal" cells, when used for nuclear transfer, will not be capable of differentiating into viable offspring.

Another preferred embodiment of the present invention is the production of nuclear transfer embryos that grow more efficiently in tissue culture. This is advantageous in that it should reduce the requisite time and necessary fusions to produce ES cells and/or offspring (if the blastocysts are to be implanted into a female surrogate). This is desirable also because it has been observed that blastocysts and ES cells resulting from nuclear transfer may have impaired development potential. While these problems may often be alleviated by alteration of tissue culture conditions, an alternative solution is to enhance embryonic development by enhancing expression of genes involved in embryonic development.

For example, it has been reported that the gene products of the Ped type, which are members of the MHC I family, are of significant importance to embryonic development. More specifically, it has been reported in the case of mouse preimplantation embryos that the Q7 and Q9 genes are responsible for the "fast growth" phenotype. Therefore, it is anticipated that introduction of DNAs that provide for the expression of these and related genes, or their human or other mammalian counterparts into donor cells, will give rise to nuclear transfer embryos that grow more quickly. This is particularly desirable in the context of cross-species nuclear transfer embryos which may develop less efficiently in tissue culture than nuclear transfer embryos produced by fusion of cells or nuclei of the same species.

In particular, a DNA construct containing the Q7 and/or Q9 gene will be introduced into donor somatic cells prior to nuclear transfer. For example, an expression construct can be constructed containing a strong constitutive mammalian promoter operably linked to the Q7 and/or Q9 genes, an IRES, one or more suitable selectable markers, e.g., neomycin, ADA, DHFR, and a poly-A sequence, e.g., bGH polyA sequence. Also, it may be advantageous to further enhance Q7 and Q9 gene expression by the inclusion of insulates. It is anticipated that these genes will be expressed early on in blastocyst development as these genes are highly conserved in different species, e.g., bovines, goats, rabbits, porcine, dogs, cats, and humans. Also, it is anticipated that donor cells can be engineered to affect other genes that enhance embryonic development. Thus, these genetically modified donor cells should produce blastocysts and preimplantation stage embryos more efficiently.

Still another aspect of the invention involves the construction of donor cells that are resistant to apoptosis, i.e., programmed cell death. It has been reported in the literature that cell death related genes are present in preimplantation stage embryos. (Adams et al, *Science*, 281(5381):1322-1326 (1998)). Genes reported to induce apoptosis include, e.g., Bad, Bok, BH3, Bik, Hrk, BNIP3, $Bim_L$, Bad, Bid, and EGL-1. By contrast, genes that reportedly protect cells from programmed cell death include, by way of example, BcL-XL, Bcl-w, Mcl-1, A1, Nr-13, BHRF-1, LMW5-HL, ORF16, Ks-Bel-2, E1B-19K, and CED-9.

Thus, donor cells can be constructed wherein genes that induce apoptosis are "knocked out" or wherein the expression of genes that protect the cells from apoptosis is enhanced or turned on during embryonic development.

For example, this can be effected by introducing a DNA construct that provides for regulated expression of such protective genes, e.g., Bcl-2 or related genes during embryonic development. Thereby, the gene can be "turned on" by culturing the embryo under specific growth conditions. Alternatively, it can be linked to a constitutive promoter.

More specifically, a DNA construct containing a Bcl-2 gene operably linked to a regulatable or constitutive promoter, e.g., PGK, SV40, CMV, ubiquitin, or beta-actin, an IRES, a suitable selectable marker, and a poly-A sequence can be constructed and introduced into a desired donor mammalian cell, e.g., human keratinocyte or fibroblast.

These donor cells, when used to produce nuclear transfer embryos, should be resistant to apoptosis and thereby differentiate more efficiently in tissue culture. Thereby, the speed and/or number of suitable preimplantation embryos produced by nuclear transfer can be increased.

Another means of accomplishing the same result is to impair the expression of one or more genes that induce apoptosis. This will be effected by knock-out or by the use of antisense or ribozymes against genes that are expressed in and which induce apoptosis early on in embryonic development. Examples thereof are identified above. Cell death genes that may be expressed in the antisense orientation include BAX, Apaf-1, and caspases. Additionally, a transgene may be introduced that encodes for methylase or demethylase in the sense or antisense orientation. DNAs that encode methylase and demethylase enzymes are well known in the art. Still alternatively, donor cells may be constructed containing both modifications, i.e., impairment of apoptosis-inducing genes and enhanced expression of genes that impede or prevent apoptosis. The construction and selection of genes that affect apoptosis, and cell lines that express such genes, is disclosed in U.S. Pat. No. 5,646,008, which patent is incorporated by reference herein. Many DNAs that promote or inhibit apoptosis have been reported and are the subject of numerous patents.

Another means of enhancing cloning efficiency is to select cells of a particular cell cycle stage as the donor cell. It has been reported that this can have significant effects on nuclear transfer efficiency. (Barnes et al, *Mol. Reprod. Devel.*, 36(1): 33-41 (1993). Different methods for selecting cells of a particular cell cycle stage have been reported and include serum starvation (Campbell et al, *Nature*, 380:64-66 (1996); Wilmut et al, *Nature*, 385:810-813 (1997), and chemical synchronization (Urbani et al, *Exp. Cell Res.*, 219(1):159-168 (1995). For example, a particular cyclin DNA may be operably linked to a regulatory sequence, together with a detectable marker, e.g., green fluorescent protein (GFP), followed by the cyclin destruction box, and optionally insulation sequences to enhance cyclin and marker protein expression. Thereby, cells of a desired cell cycle can be easily visually detected and selected for use as a nuclear transfer donor. An example thereof is the cyclin D1 gene in order to select for cells that are in G1. However, any cyclin gene should be suitable for use in the claimed invention. (See, e.g., King et al, *Mol. Biol. Cell*, Vol. 7(9):1343-1357 (1996)).

However, a less invasive or more efficient method for producing cells of a desired cell cycle stage are needed. It is anticipated that this can be effected by genetically modifying donor cells such that they express specific cyclins under detectable conditions. Thereby, cells of a specific cell cycle can be readily discerned from other cell cycles.

Cyclins are proteins that are expressed only during specific stages of the cell cycle. They include cyclin D1, D2 and D3 in G1 phase, cyclin B1 and B2 in G2/M phase and cyclin E, A and H in S phase. These proteins are easily translated and destroyed in the cytogolcytosol. This "transient" expression of such proteins is attributable in part to the presence of a "destruction box", which is a short amino acid sequence that is part of the protein that functions as a tag to direct the prompt destruction of these proteins via the ubiquitin pathway. (Adams et al, *Science*, 281 (5321):1322-1326 (1998)).

In the present invention, donor cells will be constructed that express one or more of such cyclin genes under easily detectable conditions, preferably visualizable, e.g., by the use of a fluorescent label. For example, a particular cyclin DNA may be operably linked to a regulatory sequence, together with a detectable marker, e.g., green fluorescent protein (GFP), followed by the cyclin destruction box, and optionally insulation sequences to enhance cyclin and/or marker protein expression. Thereby, cells of a desired cell cycle can be easily visually detected and selected for use as a nuclear transfer donor. An example thereof is the cyclin D1 gene which can be used to select for cells that are in G1. However, any cyclin gene should be suitable for use in the claimed invention. (See, e.g., King et al, *Mol. Biol. Cell*, Vol. 7(9):1343-1357 (1996)).

As discussed, the present invention provides different methods for enhancing nuclear transfer efficiency, preferably a cross-species nuclear transfer process. While the present inventors have demonstrated that nuclei or cells of one species when inserted or fused with an enucleated oocyte of a different species can give rise to nuclear transfer embryos that produce blastocysts, which embryos can give rise to ES cell lines, the efficiency of such process is lower than for some species donor cell/nucleus/recipient transfer Therefore, many fusions typically need to be effected to produce a blastocyst the cells of which may be cultured to produce ES cells and ES cell lines. Yet another means for enhancing the development of nuclear transfer embryos in vitro is by optimizing culture conditions. One means of achieving this result will be to culture NT embryos under conditions impede apoptosis. With respect to this embodiment of the invention, it has been found that proteases such as caspases can cause oocyte death by apoptosis similar to other cell types. (See, Jurisicosva et al, *Mol. Reprod. Devel.*, 51(3):243-253 (1998).)

It is anticipated that blastocyst development will be enhanced by including in culture media used for nuclear transfer and to maintain blastocysts or culture pre-implantation stage embryos one or more caspase inhibitors. Such inhibitors include by way of example caspase-4 inhibitor I, caspase-3 inhibitor I, caspase-6 inhibitor II, caspase-9 inhibitor II, and caspase-1 inhibitor I. The amount thereof will be an amount effective to inhibit apoptosis, e.g., 0.00001 to 5.0% by weight of medium; more preferably 0.01% to 1.0% by weight of medium. Thus, the foregoing methods may be used to increase the efficiency of nuclear transfer by enhancing subsequent blastocyst and embryo development in tissue culture.

After NT units of the desired size are obtained, the cells are mechanically removed from the zone and are then used to produce embryonic or stem-like cells and cell lines. This is preferably effected by taking the clump of cells which comprise the NT unit, which typically will contain at least about 50 cells, washing such cells, and plating the cells onto a feeder layer, e.g., irradiated fibroblast cells. Typically, the cells used to obtain the stem-like cells or cell colonies will be obtained from the inner most portion of the cultured NT unit which is preferably at least 50 cells in size. However, NT units of smaller or greater cell numbers as well as cells from other portions of the NT unit may also be used to obtain ES-like cells and cell colonies.

It is further envisioned that a longer exposure of donor cell DNA to the oocyte's cytosol may facilitate the dedifferentiation process. This can be accomplished by re-cloning, i.e., by taking blastomeres from a reconstructed embryo and fusing them with a new enucleated oocyte. Alternatively, the donor cell may be fused with an enucleated oocyte and four to six hours later, without activation, chromosomes removed and fused or injected into another, e.g., younger oocyte. Activation would occur thereafter.

The cells are maintained in the feeder layer in a suitable growth medium, e.g., alpha MEM supplemented with 10% FCS and 0.1 mM beta-mercaptoethanol (Sigma) and L-glutamine. The growth medium is changed as often as necessary to optimize growth, e.g., about every 2-3 days.

This culturing process results in the formation of embryonic or stem-like cells or cell lines. In the case of human cell/bovine oocyte derived NT embryos, colonies are observed by about the second day of culturing in the alpha MEM medium. However, this time may vary dependent upon the particular nuclear donor cell, specific oocyte and culturing conditions. One skilled in the art can vary the culturing conditions as desired to optimize growth of the particular embryonic or stem-like cells. Other suitable media are disclosed herein.

The embryonic or stem-like cells and cell colonies obtained will typically exhibit an appearance similar to embryonic or stem-like cells of the species used as the nuclear cell donor rather than the species of the donor oocyte. For example, in the case of embryonic or stem-like cells obtained by the transfer of a human nuclear donor cell into an enucleated bovine oocyte, the cells exhibit a morphology more similar to mouse embryonic stem cells than bovine ES-like cells.

More specifically, the individual cells of the human ES-line cell colony are not well defined, and the perimeter of the colony is refractive and smooth in appearance. Further, the cell colony has a longer cell doubling time, about twice that of mouse ES cells. Also, unlike bovine and porcine derived ES cells, the colony does not possess an epithelial-like appearance.

As discussed above, it has been reported by Thomson, in U.S. Pat. No. 5,843,780, that primate stem cells are SSEA-1 (−), SSEA-4 (+), TRA-1-60 (+), TRA-1-81 (+) and alkaline phosphatase (+). It is anticipated that human and primate ES cells produced according to the present methods will exhibit similar or identical marker expression.

Alternatively, that such cells are actual human or primate embryonic stem cells will be confirmed based on their capability of giving rise to all of mesoderm, ectoderm and endoderm tissues. This will be demonstrated by culturing ES cells produced according to the invention under appropriate conditions, e.g., as disclosed by Thomsen, U.S. Pat. No. 5,843,780, incorporated by reference in its entirety herein. Alternatively, the fact that the cells produced according to the invention are pluripotent will be confirmed by injecting such cells into an animal, e.g., a SCID mouse, or large agricultural animal, and thereafter obtaining tissues that result from said implanted cells. These implanted ES cells should give rise to all different types of differentiated tissues, i.e., mesoderm, ectoderm, and endodermal tissues.

The resultant embryonic or stem-like cells and cell lines, preferably human embryonic or stem-like cells and cell lines, have numerous therapeutic and diagnostic applications. Most especially, such embryonic or stem-like cells may be used for cell transplantation therapies. Human embryonic or stem-like cells have application in the treatment of numerous disease conditions.

Still another object of the present invention is to improve the efficacy of nuclear transfer, e.g., cross-species nuclear transfer by introducing mitochondrial DNA of the same species as the donor cell or nucleus into the recipient oocyte before or after nuclear transfer, before or after activation, and before or after fusion and cleavage. Preferably, if the donor cell is human, human mitochondrial DNA will be derived from cells of the particular donor, e.g., liver cells and tissue.

Methods for isolating mitochondria are well known in the art. Mitochondria can be isolated from cells in tissue culture, or from tissue. The particular cells or tissue will depend upon the particular species of the donor cell. Examples of cells or tissues that may be used as sources of mitochondria include fibroblasts, epithelium, liver, lung, keratinocyte, stomach, heart, bladder, pancreas, esophageal, lymphocytes, monocytes, mononuclear cells, cumulus cells, uterine cells, placental cells, intestinal cells, hematopoietic cells, and tissues containing such cells.

For example, mitochondria can be isolated from tissue culture cells and rat liver. It is anticipated that the same or similar procedures may be used to isolate mitochondria from other cells and tissues. As noted above, preferred source of mitochondria comprises human liver tissue because such cells contain a large number of mitochondria. Those skilled in the art will be able to modify the procedure as necessary, dependent upon the particular cell line or tissue. The isolated DNA can also be further purified, if desired, known methods, e.g., density gradient centrifugation.

In this regard, it is known that mouse embryonic stem (ES) cells are capable of differentiating into almost any cell type, e.g., hematopoietic stem cells. Therefore, human embryonic or stem-like cells produced according to the invention should possess similar differentiation capacity. The embryonic or stem-like cells according to the invention will be induced to differentiate to obtain the desired cell types according to known methods. For example, the subject human embryonic or stem-like cells may be induced to differentiate into hematopoietic stem cells, muscle cells, cardiac muscle cells, liver cells, cartilage cells, epithelial cells, urinary tract cells, etc., by culturing such cells in differentiation medium and under conditions which provide for cell differentiation. Medium and methods which result in the differentiation of embryonic stem cells are known in the art as are suitable culturing conditions.

For example, Palacios et al, *Proc. Natl. Acad. Sci., USA*, 92:7530-7537 (1995) teaches the production of hematopoietic stem cells from an embryonic cell line by subjecting stem cells to an induction procedure comprising initially culturing aggregates of such cells in a suspension culture medium lacking retinoic acid followed by culturing in the same medium containing retinoic acid, followed by transferral of cell aggregates to a substrate which provides for cell attachment.

Moreover, Pedersen, *J. Reprod. Fertil. Dev.*, 6:543-552 (1994) is a review article which references numerous articles disclosing methods for in vitro differentiation of embryonic stem cells to produce various differentiated cell types including hematopoietic cells, muscle, cardiac muscle, nerve cells, among others.

Further, Bain et al, *Dev. Biol.*, 168:342-357 (1995) teaches in vitro differentiation of embryonic stem cells to produce neural cells which possess neuronal properties. These references are exemplary of reported methods for obtaining differentiated cells from embryonic or stem-like cells. These references and in particular the disclosures therein relating to methods for differentiating embryonic stem cells are incorporated by reference in their entirety herein.

Thus, using known methods and culture medium, one skilled in the art may culture the subject embryonic or stem-like cells embryos, cultured inner cell, cell masses, morula, or blastocysts provided by cross-species nuclear transfer to obtain desired differentiated cell types, e.g., neural cells, muscle cells, hematopoietic cells, etc. In addition, the use of inducible Bcl-2 or Bcl-xl might be useful for enhancing in vitro development of specific cell lineages. In vivo, Bcl-2 prevents many, but not all, forms of apoptotic cell death that occur during lymphoid and neural development. A thorough discussion of how Bcl-2 expression might be used to inhibit apoptosis of relevant cell lineages following transfection of donor cells is disclosed in U.S. Pat. No. 5,646,008, which is herein incorporated by reference.

The subject embryonic or stem-like cells may be used to obtain any desired differentiated cell type. Therapeutic usages of such differentiated human cells are unparalleled. For example, human hematopoietic stem cells may be used in medical treatments requiring bone marrow transplantation. Such procedures are used to treat many diseases, e.g., late stage cancers such as ovarian cancer and leukemia, as well as diseases that compromise the immune system, such as AIDS. Hematopoietic stem cells can be obtained, e.g., by fusing adult somatic cells of a cancer or AIDS patient, e.g., epithelial cells or lymphocytes with an enucleated oocyte, e.g., bovine oocyte, obtaining embryonic or stem-like cells as described above, and culturing such cells under conditions which favor differentiation, until hematopoietic stem cells are obtained. Such hematopoietic cells may be used in the treatment of diseases including cancer and AIDS.

Alternatively, adult somatic cells from a patient with a neurological disorder may be fused with an enucleated animal oocyte, e.g., a primate or bovine oocyte, human embryonic or stem-like cells obtained therefrom, and such cells cultured under differentiation conditions to produce neural cell lines. Specific diseases treatable by transplantation of such human neural cells include, by way of example, Parkinson's disease, Alzheimers disease, ALS and cerebral palsy, among others. In the specific case of Parkinson's disease, it has been demonstrated that transplanted fetal brain neural cells make the proper connections with surrounding cells and produce dopamine. This can result in long-term reversal of Parkinson's disease symptoms.

To allow for specific selection of differentiated cells, donor cells may be transfected with selectable markers expressed via inducible promoters, thereby permitting selection or enrichment of particular cell lineages when differentiation is induced. For example, CD34-neo may be used for selection of hematopoietic cells, Pw1-neo for muscle cells, Mash-1-neo for sympathetic neurons, Mal-neo for human CNS neurons of the grey matter of the cerebral cortex, etc.

The great advantage of the subject invention is that it provides an essentially limitless supply of isogenic or synegenic human cells suitable for transplantation. Therefore, it will obviate the significant problem associated with current transplantation methods, i.e., rejection of the transplanted tissue which may occur because of host-vs-graft or graft-vs-host rejection. Conventionally, rejection is prevented or reduced by the administration of anti-rejection drugs such as cyclosporin. However, such drugs have significant adverse side-effects, e.g., immunosuppression, carcinogenic properties, as well as being very expensive. The present invention should eliminate, or at least greatly reduce, the need for anti-rejection drugs, such as cyclosporine, imulan, FK-506, glucocorticoids, and rapamycin, and derivatives thereof.

Other diseases and conditions treatable by isogenic cell therapy include, by way of example, spinal cord injuries, multiple sclerosis, muscular dystrophy, diabetes, liver diseases, i.e., hypercholesterolemia, heart diseases, cartilage replacement, burns, foot ulcers, gastrointestinal diseases, vascular diseases, kidney disease, urinary tract disease, and aging related diseases and conditions.

Also, human embryonic or stem-like cells produced according to the invention may be used to produce genetically engineered or transgenic human differentiated cells. Essentially, this will be effected by introducing a desired gene or genes, which may be heterologous, or removing all or part of an endogenous gene or genes of human embryonic or stem-like cells produced according to the invention, and allowing such cells to differentiate into the desired cell type. A preferred method for achieving such modification is by homologous recombination because such technique can be used to insert, delete or modify a gene or genes at a specific site or sites in the stem-like cell genome.

This methodology can be used to replace defective genes, e.g., defective immune system genes, cystic fibrosis genes, or to introduce genes which result in the expression of therapeutically beneficial proteins such as growth factors, lymphokines, cytokines, enzymes, etc. For example, the gene encoding brain derived growth factor may be introduced into human embryonic or stem-like cells, the cells differentiated into neural cells and the cells transplanted into a Parkinson's patient to retard the loss of neural cells during such disease.

Previously, cell types transfected with BDNF varied from primary cells to immortalized cell lines, either neural or non-neural (myoblast and fibroblast) derived cells. For example, astrocytes have been transfected with BDNF gene using retroviral vectors, and the cells grafted into a rat model of Parkinson's disease (Yoshimoto et al., *Brain Research*, 691:25-36, (1995)).

This ex vivo therapy reduced Parkinson's-like symptoms in the rats up to 45% 32 days after transfer. Also, the tyrosine hydroxylase gene has been placed into astrocytes with similar results (Lundberg et al., *Develop. Neurol.*, 139:39-53 (1996) and references cited therein).

However, such ex vivo systems have problems. In particular, retroviral vectors currently used are down-regulated in vivo and the transgene is only transiently expressed (review by Mulligan, *Science*, 260:926-932 (1993)). Also, such studies used primary cells, astrocytes, which have finite life span and replicate slowly. Such properties adversely affect the rate of transfection and impede selection of stably transfected cells. Moreover, it is almost impossible to propagate a large population of gene targeted primary cells to be used in homologous recombination techniques.

By contrast, the difficulties associated with retroviral systems should be eliminated by the use of human embryonic or stem-like cells. It has been demonstrated previously by the subject assignee that cattle and pig embryonic cell lines can be transfected and selected for stable integration of heterologous DNA. Such methods are described in commonly assigned U.S. Ser. No. 08/626,054, filed Apr. 1, 1996, now U.S. Pat. No. 5,905,042, incorporated by reference in its entirety. Therefore, using such methods or other known methods, desired genes may be introduced into the subject human embryonic or stem-like cells, and the cells differentiated into desired cell types, e.g., hematopoietic cells, neural cells, pancreatic cells, cartilage cells, etc.

Genes which may be introduced into the subject embryonic or stem-like cells include, by way of example, epidermal growth factor, basic fibroblast growth factor, glial derived neurotrophic growth factor, insulin-like growth factor (I and II), neurotrophin-3, neurotrophin4/5, ciliary neurotrophic factor, AFT-1, cytokine genes (interleukins, interferons, colony stimulating factors, tumor necrosis factors (alpha and beta), etc.), genes encoding therapeutic enzymes, collagen, human serum albumin, etc.

In addition, it is also possible to use one of the negative selection systems now known in the art for eliminating therapeutic cells from a patient if necessary. For example, donor cells transfected with the thymidine kinase (TK) gene will lead to the production of embryonic cells containing the TK gene. Differentiation of these cells will lead to the isolation of therapeutic cells of interest which also express the TK gene. Such cells may be selectively eliminated at any time from a patient upon gancyclovir administration. Such a negative selection system is described in U.S. Pat. No. 5,698,446, and is herein incorporated by reference.

The subject embryonic or stem-like cells, preferably human cells, also may be used as an in vitro model of differentiation, in particular for the study of genes which are involved in the regulation of early development.

Also, differentiated cell tissues and organs using the subject embryonic or stem-like cells may be used in drug studies.

Further, the subject cells may be used to express recombinant DNAs.

Still further, the subject embryonic or stem-like cells may be used as nuclear donors for the production of other embryonic or stem-like cells and cell colonies.

Also, cultured inner cell mass, or stem cells, produced according to the invention may be introduced into animals, e.g., SCID mice, cows, pigs, e.g., under the renal capsule or intramuscularly and used to produce a teratoma therein. This teratoma can be used to derive different tissue types. Also, the inner cell mass produced by X-species nuclear transfer may be introduced together with a biodegradable, biocompatible polymer matrix that provides for the formation of 3-dimensional tissues. After tissue formation, the polymer degrades, ideally just leaving the donor tissue, e.g., cardiac, pancreatic, neural, lung, liver. In some instances, it may be advantageous to include growth factors and proteins that promote angiogenesis. Alternatively, the formation of tissues can be effected totally in vitro, with appropriate culture media and conditions, growth factors, and biodegradable polymer matrices. The invention further encompasses screening different combinations of hormones and/or growth factors to identify those that induce the differentiation of cultured inner cell masses, morula, blastocysts or cells derived therefrom into desired cell lineages. Alternatively, differentiation may take place spontaneously upon removal of a cross-species embryo provided according to the invention from a future layer.

In order to more clearly describe the subject invention, the following examples are provided.

Example 1

Materials and Methods

Donor Cells for Nuclear Transfer

Epithelial cells were lightly scraped from the inside of the mouth of a consenting adult with a standard glass slide. The cells were washed off the slide into a petri dish containing phosphate buffered saline without Ca or Mg. The cells were pipetted through a small-bore pipette to break up cell clumps into a single cell suspension. The cells were then transferred into a microdrop of TL-HEPES medium containing 10% fetal calf serum (FCS) under oil for nuclear transfer into enucleated cattle oocytes.

Nuclear Transfer Procedures

Basic nuclear transfer procedures have been described previously. Briefly, after slaughterhouse oocytes were matured in vitro the oocytes were stripped of cumulus cells and enucleated with a beveled micropipette at approximately 18 hours post maturation (hpm). Enucleation was confirmed in TL-HEPES medium plus bisbenzimide (Hoechst 33342, 3 µg/ml; Sigma). Individual donor cells were then placed into the perivitelline space of the recipient oocyte. The bovine oocyte cytoplasm and the donor nucleus (NT unit) are fused together using electrofusion techniques. One fusion pulse consisting of 90 V for 15 µsec was applied to the NT unit. This occurred at 24 hours post-initiation of maturation (hpm) of the oocytes. The NT units were placed in CR1aa medium until 28 hpm.

The procedure used to artificially activate oocytes has been described elsewhere. NT unit activation was at 28 hpm. A brief description of the activation procedure is as follows: NT units were exposed for four min to ionomycin (5 µM; Cal-Biochem, La Jolla, Calif.) in TL-HEPES supplemented with 1 mg/ml BSA and then washed for five min in TL-HEPES supplemented with 30 mg/ml BSA. The NT units were then transferred into a microdrop of CR1aa culture medium containing 0.2 mM DMAP (Sigma) and cultured at 38.5° C. 5% $CO_2$ for four to five hours. The NT units were washed and then placed in a CR1aa medium plus 10% FCS and 6 mg/ml BSA in four well plates containing a confluent feeder layer of mouse embryonic fibroblasts (described below). The NT units were cultured for three more days at 38.5° C. and 5% $CO_2$. The culture medium was changed every three days until day 12 after the time of activation. At this time NT units reaching the desired cell number, i.e., about 50 cell number, were mechanically removed from the zona and used to produce embryonic cell lines. A photograph of an NT unit obtained as described above is contained in FIG. 1.

Fibroblast Feeder Layer

Primary cultures of embryonic fibroblasts were obtained from 14-16 day old murine fetuses. After the head, liver, heart and alimentary tract were aseptically removed, the embryos were minced and incubated for 30 minutes at 37° C. in pre-warmed trypsin EDTA solution (0.05% trypsin/0.02% EDTA; GIBCO, Grand Island, N.Y.). Fibroblast cells were plated in tissue culture flasks and cultured in alpha-MEM medium (BioWhittaker, Walkersville, Md.) supplemented with 10% fetal calf serum (FCS) (Hyclone, Logen, Utah), penicillin (100 IU/ml) and streptomycin (50 µl/ml). Three to four days after passage, embryonic fibroblasts, in 35×10 Nunc culture dishes (Baxter Scientific, McGaw Park, Ill.), were irradiated. The irradiated fibroblasts were grown and maintained in a humidified atmosphere with 5% $CO_2$ in air at 37° C. The culture plates which had a uniform monolayer of cells were then used to culture embryonic cell lines.

Production of Embryonic Cell Line.

NT unit cells obtained as described above were washed and plated directly onto irradiated feeder fibroblast cells. These cells included those of the inner portion of the NT unit. The cells were maintained in a growth medium consisting of alpha MEM supplemented with 10% FCS and 0.1 mM beta-mercaptoethanol (Sigma). Growth medium was exchanged every two to three days. The initial colony was observed by the second day of culture. The colony was propagated and exhibits a similar morphology to previously disclosed mouse embryonic stem (ES) cells. Individual cells within the colony are not well defined and the perimeter of the colony is refractile and smooth in appearance. The cell colony appears to have a slower cell doubling time than mouse ES cells. Also, unlike bovine and porcine derived ES cells, the colony does not have an epithelial appearance thus far. FIGS. 2 through 5 are photographs of ES-like cell colonies obtained as described, supra.

Production of Differentiated Human Cells

The human embryonic cells obtained are transferred to a differentiation medium and cultured until differentiated human cell types are obtained.

Results

Table 1. Human cells as donor nuclei in NT unit production and development.

TABLE 1

| Cell type | No. NT units made | No. NT units 2 cell stage (%) | No. NT units to 4–16 cell stage (%) | No. NT units to 16 – 400 cell stage (%) |
|---|---|---|---|---|
| lymphocytes oral cavity | 18 | 12 (67%) | 3 (17%) | 0 |
| epithelium | 34 | 18 (53%) | 3 (9%) | 1 (3%) |
| adult fibroblasts | 46 | 4 (9%) | 12 (4 cell; 26%) 8 (8–16 cells; 17.4%) | — |

The one NT unit that developed a structure having greater than 16 cells was plated down onto a fibroblast feeder layer. This structure was attached to the feeder layer and started to propagate forming a colony with a ES cell-like morphology (See, e.g., FIG. 2). Moreover, although the 4 to 16 cell stage structures were not used to try and produce an ES cell colony, it has been previously shown that this stage is capable of producing ES or ES-like cell lines (mouse, Eistetter et al., *Devel Growth and Differ.*, 31:275-282 (1989); *Bovine*, Stice et al., 1996)). Therefore, it is expected that 4-16 cell stage NT units should also give rise to embryonic or stem-like cells and cell colonies.

Also, similar results were obtained upon fusion of an adult human keratinocyte cell line with an enucleated bovine oocyte, which was cultured in media comprising ACM, uridine, glucose, and 1000 IU of LIF. Out of 50 reconstructed embryos, 22 cleaved and one developed into a blastocyst at about day 12. This blastocyst was plated and the production of an ES cell line is ongoing.

Example 2

A. Mitochondria Isolation Protocol from a Cell

This Example relates to isolation of mitochondria and use thereof to enhance the efficiency of cross-species nuclear transfer. The number of mitochondria per cell varies from cell line to cell line. For example, mouse L cells contain ~100 mitochondria per cell, whereas there are at least twice that number in HeLa cells. The cells are swollen in a hypotonic buffer and ruptured with a few strokes in a Dounce homogenizer using a tight-fitting pestle, and the mitochondria are isolated by differential centrifugation.

The solutions, tubes, and homogenizer should be pre-chilled on ice. All centrifugation steps are at 40□C. This protocol is based on starting with a washed cell pellet of 1-2 ml. The cell pellet is resuspended in 11 ml of ice-cold RSB and transferred to a 16 ml Dounce homogenizer.

RSB Buffer

RSB (A hypotonic buffer for swelling the tissue culture cells)

10 mM NaCl 1.5 mM $MgCl_2$ 10 mM Tris-HCl, pH 7.5

$MgCl_2$

The cells are allowed to swell for five to ten minutes. The progress of the swelling is maintained using a phase contrast microscope. The swollen cells are replaced, preferably by several strokes with a pestle. Immediately after, 8 ml of 2.5× MS buffer are added to give a final concentration of 1×MS. The top of the homogenizer is then covered with Parafilm and mixed by inverting a couple of times.

2.5×MS Buffer 525 mM mannitol

175 Mm sucrose 12.5 mM ris-HCl, pH 7.5

215 mM EDTA pH 7.5

1×MS Buffer 210 mM mannitol 70 mM Sucrose 5 mM Tris-HCl, pH 7.5

1 mM EDTA, pH 7.5

MS Buffer is an iso-osmotic buffer to maintain the tonicity of the organelles and prevent agglutination.

Thereafter, the homogenate is transferred to a centrifuge tube for differential centrifugation. The homogenizer is rinsed with a small amount of MS buffer and added to the homogenate. The volume is brought to 30 ml with MS buffer. The homogenate is then centrifuged at 1300 g for five minutes to remove nuclei, unbroken cells, and large membrane fragments. The supernatant is then poured into a clean centrifuge tube. The nuclear spin-down is repeated twice. The supernatant is then transferred to a clean centrifuge tube and a pellet containing the mitochondria is centrifuged at 17,000 g for 15 minutes. The supernatant is discarded and the inside of the tube wiped with a Kimwipe. The mitochondria is washed by re-suspending the pellet in 1×MS and repeating the 17,000 g sedimentation. The supernatant is discarded and the pellet is resuspended in a buffer. Mitochondria can be stored at −80°C. for prolonged periods, e.g., up to a year, but preferably will be used shortly thereafter for NT.

This basic protocol can be modified. In particular, it may be desirable to further isolate mitochondrial DNA and us same for NT. In such case, contamination with nuclei, not small organelles, potentially is a problem and the following modifications may be made. For example, the cells may be harvested in stationary growth phase when the fewest cells are actively dividing, and $CaCl_2$ substituted for $MgCl_2$ in the RSB to stabilize the nuclear membrane. The washing of the mitochondrial pellet is omitted as is the density gradient purification. Instead, the mitochondrial pellet is simply resuspended and lysed, and the mitochondrial DNA purified from any remaining nuclear DNA. As noted, suitable methods for purifying mitochondria and mitochondrial DNA are well known in the art.

Homogenization works best if the cells are resuspended in at least 5-10× the volume of the cell pellet and if the cell suspension fills the homogenizer at least half full. Press the homogenizer pestle straight down the tube, maintaining a firm, steady pressure. The Dounce homogenizer disrupts swollen tissue culture cells by pressure change. As the pestle is pressed down, pressure around the cell increases; when the cell slips past the end of the pestle, the sudden decrease in pressure causes the cell to rupture. If the pestle is very tight fitting, there may be some mechanical breakage as well.

B. Isolation of Mitochondria from Tissue

A mitochondrial isolation protocol is selected based on the particular tissue. For example, the homogenization buffer should be optimized for the tissue, and the optimal way to homogenize the tissue utilized. Suitable methods are well known in the art.

Rat liver is the most frequently used tissue for mitochondrial preparations because it is readily available, is easy to homogenize, and the cells contain a large number of mitochondria (1000-2000 per cell). For example, a motor-driven, Teflon and glass Potter-Elvehjem homogenizer can be used homogenize rat liver. Alternatively, if the tissue is soft enough, a Dounce homogenizer with a loose pestle can be used. The yield and purity of the mitochondrial preparation is influenced by the method of preparation, speed of preparation, and the age and physiological condition of the animal. As noted, methods of purifying mitochondria are well known.

Preferably, the buffer, tubes, and homogenizer will be pre-chilled. Pre-chilling a glass and Teflon type homogenizer creates the proper gap between the tube and pestle. The centrifugation steps are preferably effected at 40°C.

Essentially, the process will comprise removal of the liver, taking care not to rupture the gall bladder. This is placed in a beaker on ice and any connective tissue is removed. The tissue is recognized and returned to the beaker, e.g., using very sharp scissors, a scalpel, or razor blade, mince it into 1-2 slices. The pieces are then rinsed, preferably twice, with homogenization buffer (1×MS) to remove most of the blood, and the tissue transferred to the homogenizer tube. Enough homogenization buffer if added to prepare a 1:10 (w/v) homogenate.

Use of Isolated Mitochondria or Mitochondrial DNA to Enhance NT Efficacy

It is theorized by the inventors that the efficacy of cross-species nuclear transfer may be enhanced by introduction of mitochondria or mitochondrial DNA at the same species as donor cell or nucleus. Thereupon, the nucleus DNA of resultant NT units will be species compatible.

Mitochondria isolated by the above or other known procedures are incorporated, typically by injection, into any of the following (in the case of human donor cell/bovine oocyte nuclear transfer):

(i) non-activated, non-enucleated bovine oocytes;
(ii) non-activated, enucleated bovine oocytes;
(iii) activated, enucleated bovine oocytes;
(iv) non-activated, fused (with human donor cell or nucleus) bovine oocytes;
(v) activated, fused and cleaved reconstructed (cow oocyte/ human cell) embryo; or
(vi) activated, fused one cell reconstructed (cow oocyte/ human cell) embryo.

The same procedures will enhance other cross-species NTs. Essentially, mitochondria will again be introduced into any of (i)-(vi) of the same species as the donor cell or nucleus, and the oocyte will be of a different species origin. Generally about 1 to 200 picoliters of mitochondrial suspension are injected into any of the above. The introduction of such mitochondria will result in NT units wherein the mitochondrial and donor DNA are compatible.

Example 3

Another method for improving the efficacy of the cross-species nuclear transfer comprises the fusion of one or more enucleated somatic cells, typically human (of the same species as donor cell or nucleus), with any of the following:

(i) non-activated, non-enucleated (e.g., bovine) oocyte;
(ii) non-activated, enucleated (e.g., bovine) oocyte;
(iii) activated, enucleated (e.g., bovine) oocyte;
(iv) non-activated, fused (with human cell) oocyte (typically bovine);
(v) activated, fused and cleaved reconstructed (e.g., cow oocyte/human cell) embryo;
(vi) activated, fused one cell reconstructed (cow oocyte/ human cell) embryo; or
(vii) non-activated, fused (e.g., with human cell) oocyte (typically bovine oocyte).

Fusion is preferably effected by electrical pulse or by use of Sendai virus. Methods for producing enucleated cells (e.g., human cells) are known in the art. A preferred protocol is set forth below.

Enucleation Procedures:

Methods for the large-scale enucleation of cells with cytochalasin B are well known in the art. Enucleation is preferably effected using the monolayer technique. This method uses small numbers of cells attached to the growth surface of a culture disc and is ideal if limited numbers of donor cells are available. Another suitable procedure, the gradient technique, requires centrifugation of cells through Ficoll gradients and is best suited for enucleation of large number ($>10^7$) of cells.

Monolayer Technique. The monolayer technique is ideal for virtually any cell which grows attached to the growth surface.

Polycarbonate or polypropylene 250-ml wide-mouth centrifuge bottles with screw-top caps are sterilized by autoclaving. The caps preferably are autoclaved separately from the bottle to prevent damage to the centrifuge bottle. The bottle are prepared for the enucleation procedure by the sterile addition of 30 ml DMEM, 2 ml bovine serum, and 0.32 ml cytochalasin B (1 mg/ml) to each. The caps are placed on the bottles, and the bottles are maintained at 370° prior to use.

The cells to be enucleated (from a few hundred to ~$10^5$ cells) are seeded on a culture dish (35×15 mm; Nunc Inc., Naperville, Ill.). Typically, the cells are grown for at least twenty-four hours on the dishes to promote maximal attachment to the growth surface. Preferably, the cells are prevented from becoming confluent. The culture dish is prepared for centrifugation by wiping the outside of the bottom half of the dish (containing the cells) with 70% (v/v) ethanol for the purpose of sterilization. Alternatively, the dish can be kept sterile during cell culturing by maintaining it within a larger, sterile culture dish. The medium is removed from the dish and the dish (without top) is placed upside down within the centrifuge bottle.

The rotor (GSA, DuPont, Wilmington, Del.) and centrifuge are preferably pre-warmed to 37° by centrifugation for 30-45 minutes at 8000 rpm. The HS-4 swinging-bucket rotor (DuPont) can alternatively be used. The optimal time and speed of centrifugation varies for each cell type. For myoblasts and fibroblasts, the centrifuge bottle with the culture dish is placed in the pre-warmed rotor and centrifuged for approximately 20 minutes (interval between the time when the rotor reaches the desired speed and the time when the centrifuge is turned off). Preferably, speeds of 6500 to 7200 rpm are used.

After centrifugation, the centrifuge bottle is removed from the rotor, and the culture plate is removed from the bottles with forceps. A small amount of medium is maintained in the plate to keep the cells moist in order to maintain cell viability. The outside of the dish, including the top edge, is wiped with a sterile wiper, then moistened with 95% (v/v) ethanol, to remove any medium and to dry it. A sterile top is placed onto the dish. If the enucleated cells are not going to be used immediately, complete culture medium (medium supplemented with the appropriate concentration of serum) should be added to the dish, and the cells placed in a $CO_2$ incubator. The resultant enucleated cells (karyoplast) are fused with any of (i)-(viii) above.

While the present invention has been described and illustrated herein by reference to various specific materials, procedures, and examples, it is understood that the invention is not restricted to the particular material, combinations of materials, and procedures selected for that purpose. Numerous variations of such details can be implied and will be appreciated by those skilled in the art.

Example 4

Protocol for the Derivation of Human Stem Cells using Cross Species Nuclear Transfer with Rabbit Eggs and Human Somatic Cells Superovulation:
1—Super ovulate New Zealand does age 8-12 months using consecutive injections of FSH, the first two 0.3 mgr and the last four, 0.4 mgr twelve hours apart.
2—12 hrs after the last FSH injection, a single i.v. injection of 100 IU of hCG is given.

Oocyte Collection:
1—12 to 24 hrs after hCG injection, flush oviducts using warm (37° C.) DPBS+1% bovine serum albumin (BSA) or HTF with 1% human serum albumin (HTF-HSA).
2—Search eggs in a dissecting microscope and placed in transport media—DPBS+1% bovine serum albumin (BSA) or HTF with 1% BSA (HTF-BSA).
3—Transport to the laboratory at 38.50° C.

Egg Stripping:
1—Pick up oocytes with a pipette and place in ~1 ml of hyaluronidase (1 mgr in HTF-BSA) solution in a 15 ml conical tube.
2—Vortex for 5 minutes at a setting of 6. Pour ~5 ml HTF-BSA into conical tube containing oocytes.
3—Swirl and pour into a 60 mm bacterial plate. Repeat rinse and place plate on a dissecting scope.
4—Allow oocytes to settle.
5—Swirl plate to center oocytes.
6—Pick up all oocytes and place in a second dish of HTF-BSA.
7—Center oocytes again, pick up with a pipette and place in a dish of M199+10% fetal calf serum (FCS). Incubate at 38.5° C. and 5% $CO_2$ in air until use.

Oocyte Enucleation:
1—Pipette 2 to 4, 100-200 µl, drops of manipulation media (HTF-BSA) onto a 100 mm bacterial plate. Use the pipette tip to spread out and flatten the drops.
2—Pipette enough mineral oil on top of the drops until they are covered evenly.
3—Place the plate onto the stage of the inverted scope. Position one drop directly over the middle of the stage. Set the magnification at its lowest setting.
4—Fill the tubing between the manipulators and the opening for the manipulation needles with water. Be sure there are no air bubbles in the tubing.
5—Clean the needles: Make a 5 ml syringe with a blunted 18G needle. Connect this to a short piece of the same tubing as used for manipulation. Use this to aspirate glass-cleaning solution through one glass manipulation needle. Then place the needle tip into water that has been brought to a boil. Aspirate multiple drops of hot water to rinse out the cleaning solution and any remaining debris. Repeat with the other glass needle. The rinsing apparatus can be saved and used repeatedly.
6—Fill a cleaned, rinsed enucleation needle and holding needle with Fluorinert oil. Be sure there are no air bubbles and that the needles are filled to the very end. To do this, fill a 3 ml syringe with Fluorinert. Attach a short piece of the same tubing as used for manipulation. Connect the tubing to the blunt end of the glass needle and gently depress the plunger to fill the needle. Repeat for the other glass needle.
7—One at a time, attach each needle to the filled tubing, preventing air between the connections. Position each needle over the plate, approximately over the middle of the stage, and fasten to the manipulator arms.
8—Lower the needles into a drop on the manipulation plate. Look through the eyepieces to center and fine tune the needles by rotating the needles into the position you prefer. Advance the meniscus of Fluorinert oil until it can be viewed under higher power and moves smoothly up and down the needles.
9—After setting up, rotate the plate to move the needles into a new clean drop of media.
10—The stained oocytes are removed and placed in close proximity to the enucleation tools in the manipulation plate. This is generally done by having the tools, positioned and in focus, at 40× on the inverted scope and then, while monitoring through the objective, using a pipette to deposit the oocytes near the tips of the tools.

11—For enucleation, the oocytes are visualized using an inverted microscope with an HMC objective at 200× magnification and an UV lighting system. The UV lighting system should include a UniBlitz shutter and foot pedal to shorten the length of time oocytes are exposed to UV light.

12—Each oocyte is held with the holding pipette and rotated using the enucleation needle until the metaphase plate can clearly be seen on the margin of the cytoplasm. The enucleation pipette is then inserted through the zona pellucida to a position near the chromosomes and the metaphase plate is aspirated along with a minimum of cytoplasm. The total volume of cytoplasm should not exceed the length of the bevel of the enucleation needle.

13—UV lighting is damaging to oocytes and should only be used for a minimum of time. Oocytes should be positioned using only brief flashes of UV.

14—Successful enucleation is confirmed when the enucleation pipette is removed from the oocyte with the chromosomes visible inside the pipette tip.

15—Completed groups of oocytes are transferred to a well of M199+FCS at 37° C. and 5% $CO_2$ in air until cell transfer.

Variations:
A. The rabbit oocyte cytoplasm may be transferred to another oocyte; e.g., of a third species. Including but not limited to *Bos taurus, Bos indicus*, and *Bos gauurus. Bos gaurus* provides an advantage in that this third species has no bovine spongiform encephalopathy (prion disease). The effect of this step is to "spike" the third species oocyte with rabbit ooplasm.

B. The rabbit oocyte may be genetically modified using a zona pellucida-specific promoter driving a gene of interest, or may be modified by some other means; i.e., by injecting proteins, in order to improve reprogramming efficiency or to limit the differentiation potential of the embryo, or for other desired purposes.

Cell Transfer:
1—Remove media from human fibroblast cell line. Rinse cells with DPBS, overlay with a minimum amount of pronase solution and place on a warming plate.

2—When cells are loose (generally a few minutes), pipette to separate into a single cell suspension and transfer to a conical tube. Add 5-10 ml of M199+FCS to stop the enzymatic action of the pronase.

3—Spin the tube in the centrifuge to pellet the cells.

4—Aspirate the supernatant and re-suspend the cell pellet in a small amount of HTF-BSA. The amount will depend on the pellet size and concentration desired.

5—Transfer 5-20 µl of cell suspension to one drop on the manipulation plate.

6—20-40 enucleated oocytes are picked up and placed in the same manipulation drop as the cells. Alternatively, use separate drops for cells and oocytes, and move back and forth between the two drops.

7—Enucleated oocytes and cells are viewed at 200× on the inverted scope.

8—Individual cells are selected and picked up using the transfer pipette until there are 1-20 cells in the pipette.

9—Enucleated oocytes are held with the holding pipette and rotated with the tip of the transfer pipette, until the polar body is visible in the space closest to the tip of the transfer needle. The transfer pipette is inserted through the zona pellucida and one cell is carefully placed in the perivitelline space, next to the polar body if possible. Placement of the cell next to the polar body helps during alignment for fusion but in some cases the polar body is not present and the cell is placed anywhere in the perivitelline space.

10—When each group of oocytes is finished it is placed back in M199+FCS media at 37° C. and 5% $CO_2$ in air until fusion.

Fusion and Activation:
1—Procedure starts at 17-18 hrs after superovulation

2—Fusion is simultaneous with the first set of activation

3—Using sterile forceps, remove the fusion chamber from EtOH and immerse it in a 50 ml conical tube of sterile DBPS, rinse carefully. Transfer to a second tube of DBPS until use.

4—Place two small portions of vacuum grease ~9 cm apart on the inside surface of a 100 mm bacterial plate. Remove the fusion chamber from the DBPS and place on the plate with both ends on the vacuum grease. Press firmly into place. Flood plate with fusion media, being sure to cover chamber completely.

5—Make a manipulation tip:
  a) Pull a glass pipette on the micropipette puller using program #2 (see instruction manual for specific directions).
  b) Attach the pipette to the microforge in a vertical position.
  c) Carefully melt the tip of the pipette until it is completely closed and has a round tip.

6—Place the chamber on top of the stage warmer in the 2nd dissecting scope. The fusion machine is hooked up to the chamber with the black lead (−) attached the upper electrode and the red lead (+) attached to the lower electrode.

7—The fusion machine is set for of 3 DC pulses of 250 Kv/cm for 20 µsec. Several test pulses should be tried before NTs are fused.

8—NT units are removed from M199+FCS media and placed in HTF-BSA

9—Place eggs in a place with Mannitol media (0.3 mM) and let them settle to the bottom of the plate before moving to the fusion/activation chamber.

10—A small number of NT units are picked up (usually 4-8) from the group and placed between the electrodes in the fusion chamber. The manipulation tip is used to spin each embryo until they are all aligned with the transferred cell closest to the negative electrode and the oocyte closest to the positive electrode. A pulse is given, the embryos are removed from the fusion chamber, and are placed in M199+FCS at 37° C., 5% CO2. Alternatively, solution of from 37° C. to 38.5° C. can be used.

11—One hour later steps 8, 9 and 10 are repeated.

12—After the second set of stimulation they were incubated in 5 µgr Cycloheximide and 2 mM DMAP in M199 for one hour then, 13—washed and cultured in M199+10% FCS Embryo Culture:
1—Preparing culture plates: warmed M199 media with 10% FBS/well (alternatively, rabbit vitreous humor can be used). Overlay each well with enough mineral oil to cover media. Be sure that the mineral oil has been filtered through at least a 0.45 µm filter before use.

2—Prepared culture plates should equilibrate at 37° C. and 5% $CO_2$ in air for at least 3 hours before use. It is preferable to equilibrate them overnight. Alternatively, the plates can be equilibrated at from 37° C. to 38.5° C.

3—Remove embryos from the activation plates. Rinse 3× in HTF-BSA and place in the prepared culture plates. This is considered Day 0 of embryo development. It is preferable to place less than 50 embryos per well.

4—Incubate throughout culture at 37° C. and 5% $CO_2$ in air. Alternatively, the embryos can be incubated at from 37° C. to 38.5° C.

5—On Day 3 transfer the embryos to a fresh culture plate (prepared as above). Only the cleaved embryos should be moved. The percent cleavage should be determined and recorded at this time.

6—Evaluate for blastocyst development on days 5, 6 and 7 of culture.

7—Blastocysts should be subjected to immunosurgery.

8—All embryos that do not develop after day 13 must be recorded and discarded.

Immunosurgery:

1—Make 3-20 µl drops of pronase (protease) under oil and move the blastocysts from drop 1 to 3. Leave them in drop 3 and wait until the zona pellucida is dissolved. Look at the blastocyst constantly and as soon as the zona disappear they must be removed.

2—Rinse 6 times in HTF-BSA.

3—Make 3-20 µl drops of antibody (Sigma polyclonal against whole human serum albumin H-8765 diluted 1:3 in G2) under oil and move the blastocysts from drop 1 to 3. Leave them in drop 3 for 30 minutes.

4—Rinse 6 times in HTF-BSA

5—Make 3-20 µl drops of Guinea Pig complement diluted 1:3 in G2 under oil and move the blastocysts from drop 1 to 3. Leave them in drop 3 for 30 minutes. The blastocyst should collapse.

6—Rinse 6 times in HTF-BSA

7—Place the remaining of the embryo (ICM) in mitotically inactivated mouse feeder layer and culture with DMEM+15% FCS.

Results

Nuclear transfer was performed as described above, using somatic nuclear donor cells from a 2 year-old human donor. As of Feb. 28, 2002, six out of forty one nuclear transfer embryos had developed to the morula stage, and one was compacting, a sign of genome activation.

What is claimed is:

1. A method for producing a nuclear transfer human/rabbit blastocyst by cross-species nuclear transfer to give rise to embryonic stem-like cells comprising:
    (i) inserting a human cell or human cell nucleus into an enucleated recipient rabbit oocyte under conditions suitable for the formation of a nuclear transfer (NT) unit;
    (ii) activating the NT unit formed in step (i); and
    (iii) culturing the NT unit until the blastocyst stage to give rise to embryonic stem-like cells, wherein the embryonic stem-like cells are pluripotent.

2. The method of claim 1 which further comprises transferring the nucleus of the NT unit from step (i) into another rabbit oocyte which is enucleated before transfer of the nucleus.

3. The method of claim 1 wherein the nuclear transfer blastocyst produced by step (iii) is cultured on a feeder layer.

4. The method of claim 3 wherein the blastocyst is cultured on a fibroblast feeder layer.

* * * * *